(12) United States Patent
Feng et al.

(10) Patent No.: US 10,529,130 B2
(45) Date of Patent: Jan. 7, 2020

(54) METHODS AND SYSTEMS FOR EMISSION COMPUTED TOMOGRAPHY IMAGE RECONSTRUCTION

(71) Applicant: UIH AMERICA, INC., Houston, TX (US)

(72) Inventors: Tao Feng, Houston, TX (US); Jizhe Wang, Houston, TX (US); Hongdi Li, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 0 days.

(21) Appl. No.: 16/511,160

(22) Filed: Jul. 15, 2019

(65) Prior Publication Data

US 2019/0340813 A1    Nov. 7, 2019

Related U.S. Application Data

(60) Division of application No. 15/618,425, filed on Jun. 9, 2017, now Pat. No. 10,360,724, which is a
(Continued)

(51) Int. Cl.
*G06K 9/00*  (2006.01)
*G06T 17/20*  (2006.01)
(Continued)

(52) U.S. Cl.
CPC ............... *G06T 17/20* (2013.01); *A61B 6/00* (2013.01); *A61B 6/037* (2013.01); *A61B 6/5264* (2013.01); *G06T 2210/41* (2013.01)

(58) Field of Classification Search
None
See application file for complete search history.

(56) References Cited

U.S. PATENT DOCUMENTS 8,569,706 B2 * 10/2013 Thiruvenkadam ..... A61B 6/037
250/363.03
2011/0103664 A1   5/2011 Kovalski
(Continued)

FOREIGN PATENT DOCUMENTS

WO   2007015199 A2   2/2007
WO   2015134176 A1   9/2015

OTHER PUBLICATIONS

Extended European Search Report in European Application No. 17884856.0 dated Nov. 20, 2019, 8 pages.

*Primary Examiner* — Atiba O Fitzpatrick
(74) *Attorney, Agent, or Firm* — Metis IP LLC

(57) ABSTRACT

The present disclosure relates to a method and system for reconstructing an Emission Computed Tomography (ECT) image based on locally adaptive gating. ECT projection data relating to a subject may be obtained. The ECT projection data may correspond to a plurality of voxels in a reconstructed image domain. The ECT projection data may be divided into a plurality of frames. A plurality of intermediate images may be reconstructed according to the plurality of frames. A plurality of motion amplitudes of the plurality of voxels may be obtained based on the plurality of intermediate images. A plurality of gate numbers may be determined for the plurality of voxels based on the plurality of motion amplitudes of the plurality of voxels. A plurality of ECT images may be reconstructed based on the ECT projection data and the plurality of gate numbers.

20 Claims, 13 Drawing Sheets

Related U.S. Application Data continuation-in-part of application No. 15/386,048, filed on Dec. 21, 2016, now Pat. No. 10,255,694.

(51) Int. Cl.
*A61B 6/00* (2006.01)
*A61B 6/03* (2006.01)

(56) References Cited

U.S. PATENT DOCUMENTS

| | | |
|---|---|---|
| 2012/0051664 A1* | 3/2012 | Gopalakrishnan .... G06T 11/005 382/294 |
| 2012/0305780 A1 | 12/2012 | Thiruvenkadam et al. |
| 2015/0036905 A1 | 2/2015 | Mueller et al. |
| 2016/0324500 A1 | 11/2016 | Fan et al. |

\* cited by examiner

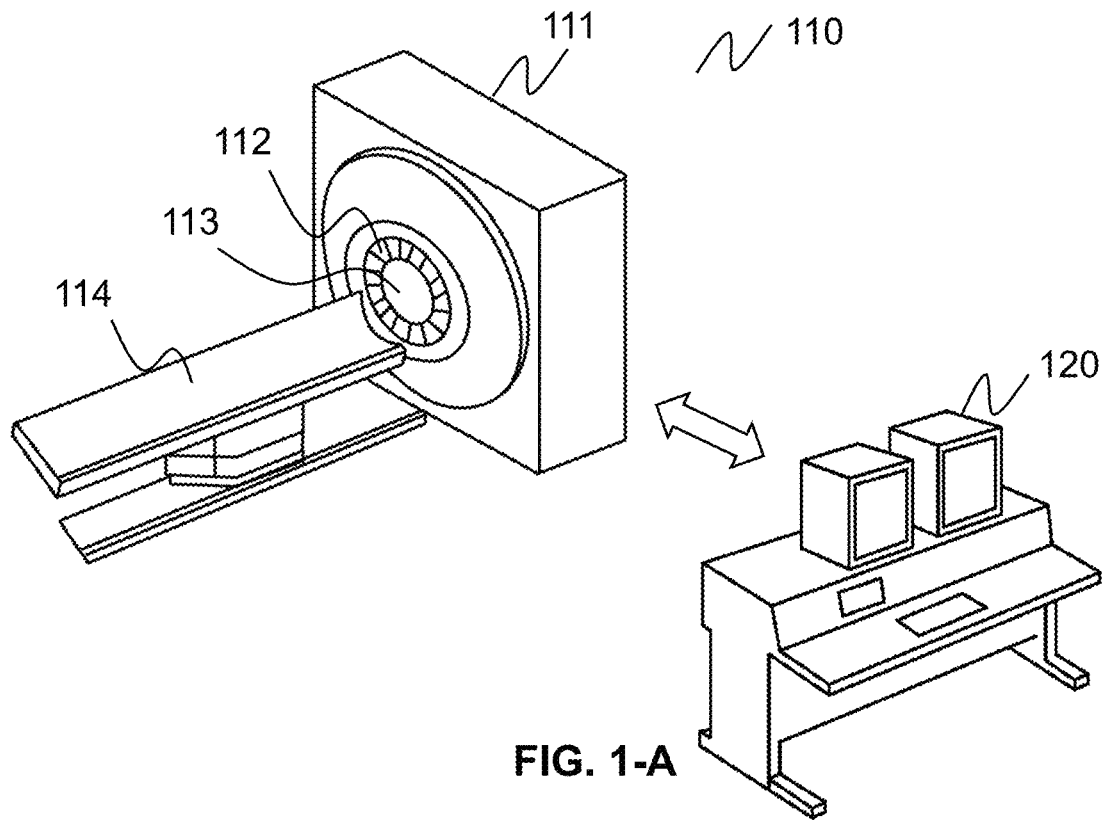
FIG. 1-A
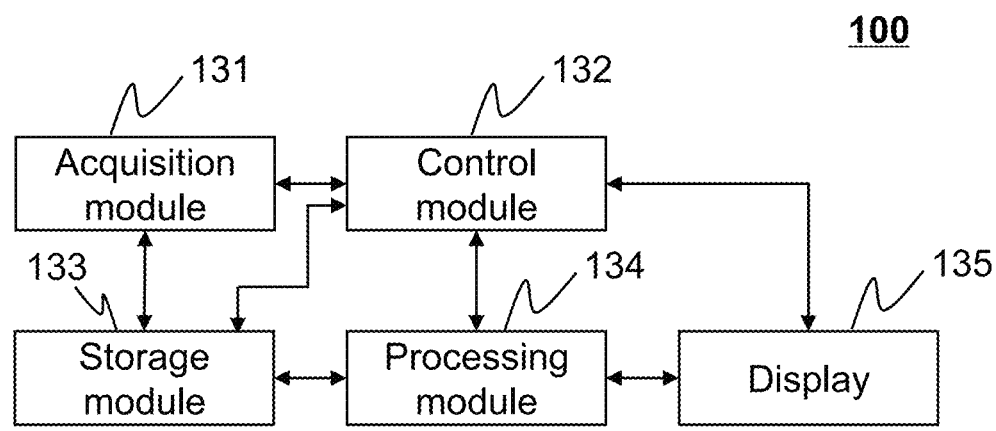
FIG. 1-B

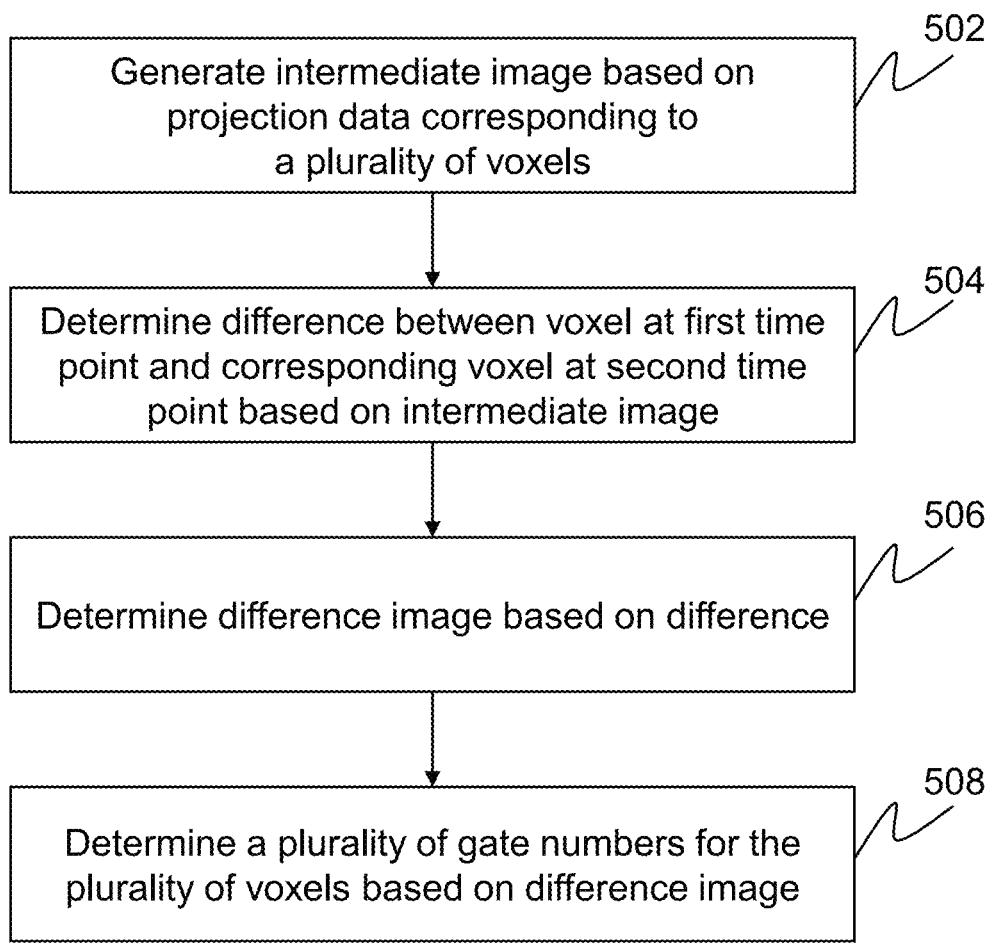
FIG. 5-A

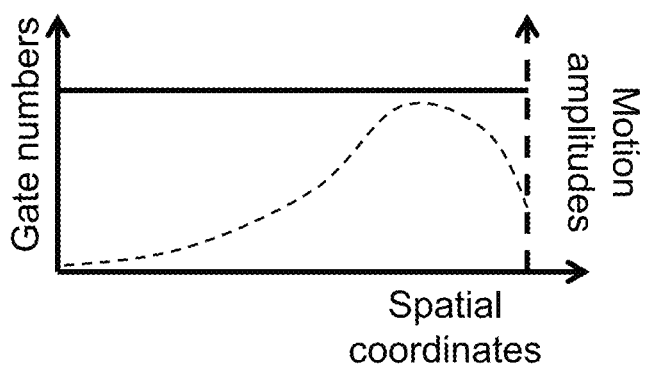
FIG. 5-B1
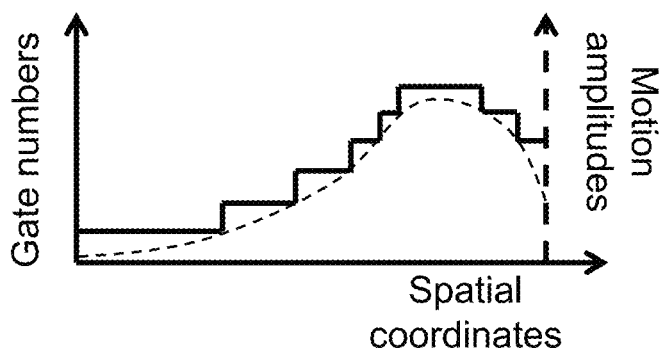
FIG. 5-B2
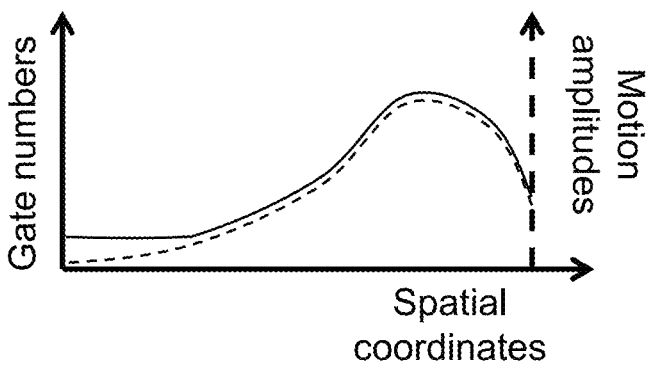
FIG. 5-B3

FIG. 7-A
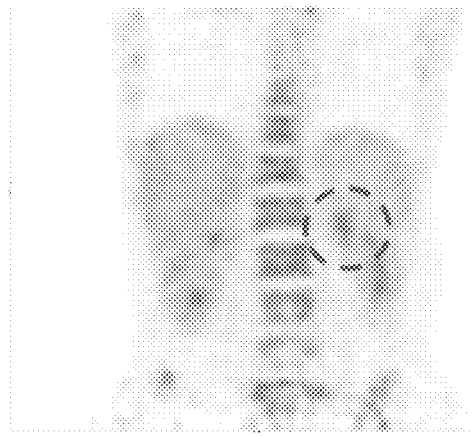
FIG. 7-B
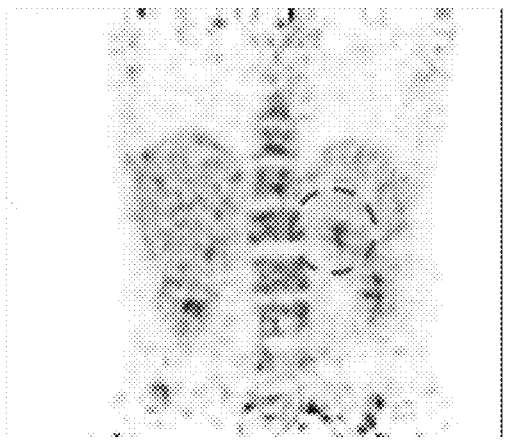
FIG. 7-C

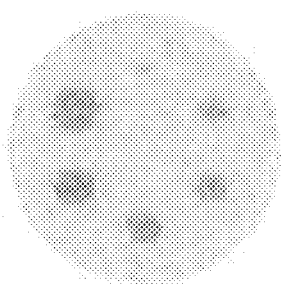
FIG. 8-A
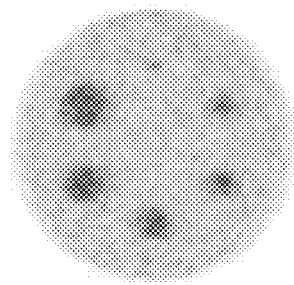 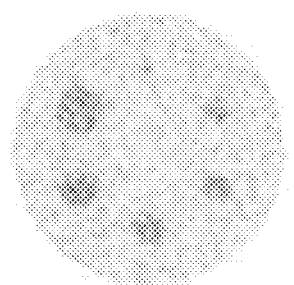
FIG. 8-B					FIG. 8-C

METHODS AND SYSTEMS FOR EMISSION COMPUTED TOMOGRAPHY IMAGE RECONSTRUCTION

CROSS-REFERENCE TO RELATED APPLICATIONS

This application is a divisional application of U.S. patent application Ser. No. 15/618,425, field on Jun. 9, 2017, which is a continuation-in-part of U.S. patent application Ser. No. 15/386,048, entitled METHODS AND SYSTEMS FOR EMISSION COMPUTED TOMOGRAPHY IMAGE RECONSTRUCTION, filed on Dec. 21, 2016, the contents of which are hereby incorporated by reference.

TECHNICAL FIELD

The present disclosure generally relates to image reconstruction, and more specifically relates to methods and systems for reconstructing a locally adaptively gated image.

BACKGROUND

Emission Computed Tomography (ECT) has been widely used in medicine for diagnosis and other purposes. A subject, such as a patient, may be scanned by a scanner to obtain medical images. When the medical imaging system is used for chest or upper abdomen examinations, respiratory motion of the lungs and/or cardiac movements of the heart of a subject may lead to motion blur in the medical images. The motion blur may be reduced by using a gating approach.

A single field of view of a total-body PET scanner may cover the entire body of a subject. Various regions of the entire body of the subject may move to various degrees during the scanning of the subject. A conventional gating approach may be inapplicable to the total-body PET scanner as it would divide the data of entire body into different frames covering different motion phases, while noticeable motions may occur only in selected regions of the body such as the chest and the abdomen. It is desirable to develop methods and systems for reconstructing data acquired by a total-body PET scanner with reduced motion blur without over-gating of a region of the subject that is not significantly affected by the motion of the subject during the scanning.

SUMMARY

A first aspect of the present disclosure relates to a method for reconstructing an Emission Computed Tomography (ECT) image. The method may be implemented on at least one machine each of which has at least one processor and storage. The method may include one or more of the following operations. ECT projection data relating to a subject may be obtained. The ECT projection data may correspond to a plurality of voxels in a reconstructed image domain. The ECT projection data may be divided into a plurality of frames. A plurality of intermediate images may be reconstructed according to the plurality of frames. A plurality of motion amplitudes of the plurality of voxels may be obtained based on the plurality of intermediate images. A plurality of gate numbers may be determined for the plurality of voxels based on the plurality of motion amplitudes of the plurality of voxels. A plurality of ECT images may be reconstructed based on the ECT projection data and the plurality of gate numbers.

A second aspect of the present disclosure relates to a system for reconstructing an Emission Computed Tomography (ECT) image. The system may include an acquisition module and a processing module. The acquisition module may obtain ECT projection data relating to a subject. The ECT projection data may correspond to a plurality of voxels in a reconstructed image domain. The processing module may include a gating control unit and a reconstruction unit. The gating control unit may divide the ECT projection data into a plurality of frames. The reconstruction unit may reconstruct a plurality of intermediate images according to the plurality of frames. The gating control unit may further determine a plurality of motion amplitudes of the plurality of voxels based on the plurality of intermediate images; and determining, based on the plurality of motion amplitudes of the plurality of voxels, a plurality of gate numbers for the plurality of voxels. The reconstruction unit may further reconstruct a plurality of ECT images based on the ECT projection data and the plurality of gate numbers.

In some embodiments, the ECT projection data may be acquired using a single-bed whole-body PET scanner. The ECT projection data may be acquired in a whole field of view (FOV). The whole field of view comprises a plurality of local VOIs. The gate numbers corresponding to at least two of the local VOIs may be different. In some embodiments, a gating area in the whole field of view may be determined based on the plurality of motion amplitudes of the plurality of voxels. The gating area may be determined based on a user input, or based on the motion amplitudes of the spatial points of the subject.

In some embodiments, the plurality of intermediate images may include a first image frame and a second image frame. The plurality of motion amplitudes of the plurality of voxels may be determined based on the first image frame and the second image frame. In some embodiments, to determine the plurality of motion amplitudes of the plurality of voxels, the first image frame and the second image frame may be registered to obtain a plurality of 3D motion vectors; and the plurality of motion amplitudes of the plurality of voxels may be determined based on the plurality of motion vectors.

In some embodiments, the registration of the first image frame and the second image frame may include one or more of the following operations. Two-dimensional image registration may be performed based on the first image frame and the second image frame. For each spatial point, a 2D motion vector in a coronal plane and a 2D motion vector in a sagittal plane may be determined based on the registration. The plurality of 3D motion vectors may be obtained based on the 2D motion vectors in a coronal plane and the 2D motion vectors in a sagittal plane. The plurality of 3D motion vectors may form a 3D motion vector field.

In some embodiments, the registration of the first image frame and the second image frame may include performing 3D image registration. Based on the 3D image registration, the plurality of 3D motion vectors may be determined. For instance, a 3D motion vector field including the plurality of 3D motion vectors may be determined based on the 3D image registration.

In some embodiments, the first image frame and the second image frame may correspond to a first involuntary motion phase and a second involuntary motion phase of the subject, respectively. The involuntary motion may be respiratory motion, cardiac motion, etc. For instance, the first involuntary motion phase and the second involuntary motion phase may correspond to an end-inspiration and an end-expiration of a respiratory motion the subject, respectively. As another example, the first involuntary motion phase and the second involuntary motion phase may correspond to an end-diastolic phase and an end-systolic phase of a cardiac motion of the subject, respectively.

A third aspect of the present disclosure relates to a method for image processing. The method may be implemented on at least one machine each of which has at least one processor and storage. The method may include one or more of the following operations. Imaging data from a scanning of a subject may be obtained. A first motion signal of a first motion type and a second motion signal of a second motion type may be obtained. The imaging data may be divided, based on the first motion signal, into groups of the first gated imaging data. A group of the first gated imaging data may correspond to a motion phase of the first motion type of the subject. A first group and a second group of the first gated imaging data may correspond to a first motion phase and a second motion phase of the first motion type of spatial points of the subject. A first gated image corresponding to the first motion phase of the first motion type may be reconstructed using the first group of first gated imaging data. A second gated image corresponding to the second motion phase of the first motion type may be reconstructed using the second group of first gated imaging data. The first gated image and the second gated image may be registered to determine a motion vector field of the first motion type. The motion vector field of the first motion type may include a plurality of motion vectors of the first motion type. A motion vector of the first motion type may indicate a motion of a spatial point of the first motion type from the first motion phase to the second motion phase. For each spatial point, a first motion amplitude may be determined based on the corresponding motion vector field of the first motion type. The imaging data may be divided, based on the second motion signal, into groups of the second gated imaging data. According to operations similar to those with respect to the groups of the first gated imaging data, for each spatial point, a second motion amplitude may be determined based on the corresponding motion vector field of the second motion type. The imaging data may be gated according to dual gating based on the first motion signal and the second motion signal. The dual gating may be based on a locally adaptive gating approach. For each spatial point, a temporal spread function may be determined based on the first motion amplitude and the second motion amplitude of the spatial point, a first resolution recovery of the first motion type, and a second resolution recovery of the second motion type. A dual gated image may be reconstructed from the locally adaptively gated imaging data and the temporal spread functions.

A fourth aspect of the present disclosure relates to a system for image processing. The system may include an acquisition module and a processing module. The acquisition module may obtain imaging data from a scanning of a subject. The acquisition module may obtain obtaining a first motion signal of a first motion type and a second motion signal of a second motion type. The processing module may include a gating control unit and a reconstruction unit. The gating control unit may divide the imaging data, based on the first motion signal, into groups of the first gated imaging data. A group of the first gated imaging data may correspond to a motion phase of the first motion type of the subject. A first group and a second group of the first gated imaging data may correspond to a first motion phase and a second motion phase of the first motion type of spatial points of the subject. The reconstruction unit may reconstruct a first gated image corresponding to the first motion phase of the first motion type using the first group of first gated imaging data and a second gated image corresponding to the second motion phase of the first motion type using the second group of first gated imaging data. The gating control unit may also register the first gated image and the second gated image to determine a motion vector field of the first motion type. The motion vector field of the first motion type may include a plurality of motion vectors of the first motion type. A motion vector of the first motion type may indicate a motion of a spatial point of the first motion type from the first motion phase to the second motion phase. The gating control unit may further, for each spatial point, determine a first motion amplitude based on the corresponding motion vector field of the first motion type, and divide the imaging data based on the second motion signal. A group of the second gated imaging data may correspond to a motion phase of the second motion type of the subject. A first group and a second group of the second gated imaging data may correspond to a first motion phase and a second motion phase of the second motion type of the spatial points of the subject. The gating control unit may determine, for each spatial point, a second motion amplitude based on the corresponding motion vector field of the second motion type according to the operations similar to those with respect to the groups of the first gated imaging data. The gating control unit may gate, according to dual gating based on the first motion signal and the second motion signal, the imaging data. The dual gating may be based on a locally adaptive gating approach. For each spatial point, the gating control unit may assess a temporal spread function based on the first motion amplitude and the second motion amplitude of the spatial point. The reconstruction unit may further reconstructing a dual gated image from the locally adaptively gated imaging data and the temporal spread functions.

In some embodiments, the first motion type corresponds to a voluntary motion, and the second motion type corresponds to an involuntary motion. In some embodiments, the involuntary motion may be a respiratory motion, a cardiac motion, etc.

In some embodiments, the registration of the first gated image and the second gated image to determine a motion vector field of the first motion type may include performing 2D image registration of the first gated image and the second gated image; determining, for each spatial point, a 2D motion vector in a coronal plane and a 2D motion vector in a sagittal plane based on the registration; and determining the motion vector field based on the 2D motion vectors in a coronal plane and a 2D motion vectors in a sagittal plane. The motion vector field may be three-dimensional.

In some embodiments, the registration of the first image frame and the second image frame may include performing 3D image registration. The motion vector field may be determined based on the 3D image registration. The motion vector field may be three-dimensional.

In some embodiments, the reconstruction of a dual gated image from the locally adaptively gated imaging data and the temporal spread functions may include determining an intra-frame motion amplitude based on a system intrinsic resolution; and determining a gate number corresponding to the second motion signal according to the locally adaptive gating approach based on the intra-frame motion amplitude.

In some embodiments, the gating control unit may further determine a gating area corresponding to the first motion signal or the second motion signal; determining a plurality of gate numbers for a plurality of voxels corresponding to spatial points included in the gating area; and determining the corresponding temporal spread functions for the plurality of voxels based on the plurality of gate numbers and the motion amplitudes of the spatial points corresponding to the first motion signal or the second motion signal. The gating area may be determined by one or more of the following operations. The second motion amplitudes of the second motion type of the spatial points may be compared with a first threshold that relates to a system intrinsic resolution. The gating area may be determined based on the comparison. In some embodiments, the gating area may be determined based on a user input.

A further aspect of the present disclosure relates to systems for performing the methods disclosed herein. A system may include at least one processor and storage for storing instructions. The instructions, when executed by the at least one processor, may cause the system to perform a method disclosed herein.

A still further aspect of the present disclosure relates to non-transitory computer readable media including executable instructions for implementing the methods disclosed herein.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a schematic diagram illustrating an exemplary ECT system according to some embodiments of the present disclosure;

FIG. 1-B is a block diagram illustrating an exemplary image processing system according to some embodiments of the present disclosure;

FIG. 5-A is a flowchart illustrating an exemplary process for determining gate numbers for reconstructing an ECT image according to some embodiments of the present disclosure;

FIG. 5-B1 through FIG. 5-B3 are diagrams illustrating exemplary gating approaches based on motion amplitudes according to some embodiments of the present disclosure;

FIG. 7-A through FIG. 7-C illustrate exemplary ECT images generated by different image reconstruction methods according to some embodiments of the present disclosure;

FIG. 8-A through FIG. 8-C illustrate exemplary ECT images generated by different image reconstruction methods according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
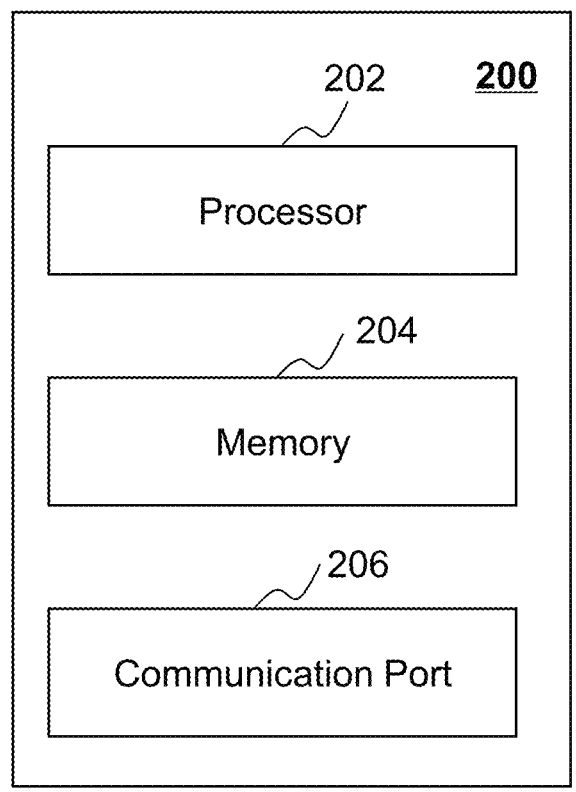
FIG. 2 is a block diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be an emission computed tomography (ECT) system, a magnetic resonance imaging (MRI) system, an ultrasonography system, a multi-modality system, or the like, or any combination thereof. The ECT system may include a positron emission tomography (PET) system, a single photon emission computed tomography (SPECT) system, etc. Exemplary multi-modality system may include a computed tomography-positron emission tomography (CT-PET) system, a magnetic resonance-positron emission tomography (MR-PET) system, etc. In some embodiments, the multi-modality imaging system may include modules and/or components for performing ECT imaging and/or related analysis.

For illustration purposes, the disclosure describes systems and methods for ECT image reconstruction. It is understood that this is for illustration purposes and not intended to limit the scope of the present disclosure.

The imaging system may reconstruct an ECT image based on a gating approach. As used herein, a gating approach may refer to that ECT data may be divided into a plurality of sections and one of the sections may be selected to be processed to generate an ECT image. For example, the imaging system may sort the ECT data acquired from a subject into a plurality of bins based on one or more gate numbers and reconstruct an ECT image based on at least one of the plurality of bins. As another example, the imaging system may reconstruct an ECT image by applying different gate numbers to the ECT data corresponding to different spatial points of a subject. In the present disclosure, "gating number," "gate number," and "a number of gates" are used interchangeably.

The following description is provided to help better understanding ECT image reconstruction methods or systems. The term "image" used in this disclosure may refer to a 2D image, a 3D image, a 4D image, or any related image data (e.g., the ECT data, projection data corresponding to the ECT data). Image data may also be referred to as imaging data. The image data may correspond to a distribution of an ECT tracer molecules within the subject. As used herein, the ECT tracer may refer to a substance that may undergo certain changes under the influence of an activity and/or functionality within the subject, whose activity and/or functionality may be visualized and/or studied. This is not intended to limit the scope the present disclosure. For persons having ordinary skills in the art, a certain amount of variations, changes, and/or modifications may be deducted under guidance of the present disclosure. Those variations, changes, and/or modifications do not depart from the scope of the present disclosure.

FIG. 1-A is a schematic diagram illustrating an exemplary ECT system according to some embodiments of the present disclosure. The ECT system may include an ECT scanner 110 and a host computer 120. ECT scanner 110 may include a gantry 111, one or more detectors 112, a detecting region 113, and a subject table 114.

Detector 112 may detect radiation events (e.g., gamma photons) emitted from detecting region 113. In some embodiments, detector 112 may include a plurality of detector units which may forms a field of view of a total-body PET scanner. The detector units may be implemented in any suitable manner, for example, a ring, a rectangle, or an array. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. Subject table 114 may position a subject in detecting region 113.

In some embodiments, the detected radiation events may be stored or archived in a storage (e.g., a storage device in host computer 120), displayed on a display (e.g., a screen on host computer 120), or transferred to any relating device (e.g., an external database). In some embodiments, a user may control ECT scanner 110 via host computer 120.

Further, while not shown, the ECT system may be connected to a network (e.g., a telecommunications network, a local area network (LAN), a wireless network, a wide area network (WAN) such as the Internet, a peer-to-peer network, a cable network, etc.) for communication purposes.

It should be noted that the above description of the ECT system is merely provided for the purposes of illustration, and not intended to limit the scope of the present disclosure. For persons having ordinary skills in the art, multiple variations and modifications may be made under the teachings of the present disclosure. For example, the assembly and/or function of the ECT system may be varied or changed according to specific implementation scenarios. Merely by way of example, some other components may be added into the ECT system, such as a patient positioning module, a gradient amplifier module, and other devices or modules.

FIG. 1-B is a block diagram illustrating an exemplary image processing system 100 according to some embodiments of the present disclosure. Image processing system 100 may be implemented via host computer 120. As illustrated in FIG. 1-B, image processing system 100 may include an acquisition module 131, a control module 132, a storage module 133, a processing module 134, and a display 135.

Acquisition module 131 may acquire or receive ECT data. The ECT data may include SPECT data, PCT data, or CT data. The ECT data may be a data set. In some embodiments, the ECT data may be list-mode data or sinogram data. Merely by way of example with reference to a PET system, acquisition module 131 may acquire or receive PET data. In some embodiments, during a PET scan or analysis, PET tracer (also referred to as "PET tracer molecules") are first introduced into the subject before an imaging process begins. During the PET scan, the PET tracer molecules may emit positrons, namely the antiparticles of electrons. A positron has the same mass and the opposite electrical charge as an electron, and it undergoes an annihilation (also referred to as an "annihilation event" or a "coincidence event") with an electron (that may naturally exist in abundance within the subject) as the two particles collide. An electron-positron annihilation may result in two 511 keV gamma photons, which, upon their own generation, begin to travel in opposite directions with respect to one another. The line connecting the two gamma photons may be referred to as a "line of response (LOR)." Acquisition module 131 may obtain the trajectory and/or information of the gamma photons (also referred to as the "PET data"). For example, the PET data may include a list of annihilation events, transverse and longitudinal positions of the LORs, or the like, or a combination thereof. In some embodiments, the PET data may be used to determine the locations and/or the concentration distribution of the PET tracer molecules within the subject.

In some embodiments, the PET tracer may include carbon (11C), nitrogen (13N), oxygen (15O), fluorine (18F), or the like, or a combination thereof. In some embodiments, for a SPECT system, a SPECT tracer may be introduced into the subject. The SPECT tracer may include technetium-99m, iodine-123, indium-111, iodine-131, or the like, or a combination thereof. Accordingly, in some embodiments, the PET tracer or SPECT tracer of the present disclosure may be organic compounds containing one or more of such isotopes. These tracers are either similar to naturally occurring substances or otherwise capable of interacting with the functionality or activity of interest within the subject. Hence, distributional information of the tracer may be reliably used as an indicator of the subject functionality. In some embodiments, the PET tracer and the SPECT tracer may be collectively referred to as "ECT tracer."

Control module 132 may generate a control parameter for acquisition module 131, storage module 133, processing module 134, and display 135. For example, control module 132 may control acquisition module 131 as to whether to acquire a signal, or the time when a signal acquisition may occur. As another example, control module 132 may control processing module 134 to select different algorithms to process the ECT data acquired by acquisition module 131. In some embodiments, control module 132 may receive a real-time or a predetermined command provided by a user (e.g., a doctor) and adjust acquisition module 131, and/or processing module 134 to take images of a subject according to the received command. In some embodiments, control module 132 may communicate with the other modules in image processing system 100 for exchanging information or data.

Storage module 133 may store the acquired ECT data, the control parameters, the processed ECT data, or the like, or a combination thereof. In some embodiments, storage 133 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, storage 133 may store one or more programs and/or instructions that may be executed by the processor(s) of image processing system 100 to perform exemplary methods described in this disclosure. For example, storage 133 may store program(s) and/or instruction(s) executed by the processor(s) of image processing system 100 to acquire ECT data, reconstruct an image based on the ECT data, or display any intermediate result or a resultant image.

Processing module 134 may process different kinds of information received from different modules in image processing system 100. In some embodiments, processing module 134 may process the ECT data acquired by acquisition module 131, or retrieved from storage module 133. In some embodiments, processing module 134 may reconstruct ECT images based on the ECT data, generate reports including one or more ECT images and/or other related information, or the like. For example, processing module 134 may process the ECT data based on a gating approach and reconstruct an ECT image based on the gated ECT data. As another example, processing module 134 may determine a plurality of gate numbers for the ECT data corresponding to a plurality of spatial points of the subject (e.g., chest, back, or the like).

Display 135 may display any information relating to image processing system 100. The information may include programs, software, algorithms, data, text, number, images, voice, or the like, or any combination thereof. In some embodiments, display 135 may include a liquid crystal display (LCD), a light emitting diode (LED) based display, a flat panel display, a cathode ray tube (CRT), a touch screen, or the like, or a combination thereof. The touch screen may include, for example, a resistance touch screen, a capacity touch screen, a plasma touch screen, a vector pressure sensing touch screen, an infrared touch screen, or the like, or a combination thereof. In some embodiments, display 135 may have a window for selecting a gating area of a subject.

In some embodiments, one or more modules illustrated in FIG. 1-B may be implemented in at least part of the exemplary ECT system illustrated in FIG. 1-A. For example, acquisition module 131, control module 132, storage module 133, processing module 134, and/or display or display device 135 may be integrated into a console (not shown). Via the console, a user may set parameters for scanning, control the imaging procedure, control a parameter of the reconstruction of an image, view the reconstructed images, etc. In some embodiments, the console may be implemented via host computer 120.

FIG. 2 is a block diagram illustrating exemplary hardware and software components of computing device 200 on which image processing system 100 may be implemented according to some embodiments of the present disclosure. In some embodiments, computing device 200 may include a processor 202, a memory 204, and a communication port 206.

Processor 202 may execute computer instructions (program code) and perform functions of processing module 134 in accordance with techniques described herein. Computer instructions may include routines, programs, objects, components, data structures, procedures, modules, and functions, which perform particular functions described herein. For example, processor 202 may process the data or information received from acquisition module 131, control module 132, storage module 133, processing module 134, or any other component of image processing system 100. In some embodiments, processor 202 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, processor 202 may include a microcontroller to process the ECT data from ECT scanner 110 for image reconstruction.

Memory 204 may store the data or information received from acquisition module 131, control module 132, storage module 133, processing module 134, or any other component of image processing system 100. In some embodiments, memory 204 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, memory 204 may store one or more programs and/or instructions to perform exemplary methods described in the present disclosure. For example, memory 204 may store a program for processing module 134 for reconstructing an ECT image based on the ECT data.

Communication port 206 may transmit to and receive information or data from acquisition module 131, control module 132, storage module 133, processing module 134 via network. In some embodiments, communication port 206 may include a wired port (e.g., a Universal Serial Bus (USB) port, a High Definition Multimedia Interface (HDMI) port, or the like) or a wireless port (a Bluetooth port, an infrared interface, a WiFi port, or the like).

Figure 3:
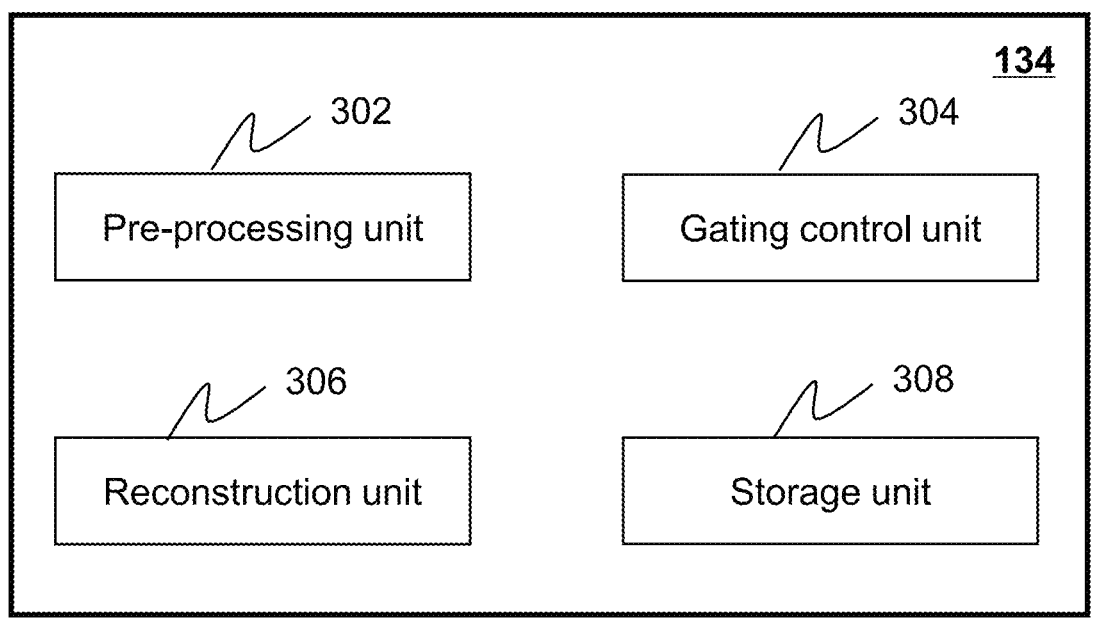
FIG. 3 is a block diagram illustrating an exemplary processing module according to some embodiments of the present disclosure.

FIG. 3 is a block diagram illustrating an exemplary processing module 134 according to some embodiments of the present disclosure. Processing module 134 may include a pre-processing unit 302, a gating control unit 304, a reconstruction unit 306, and a storage unit 308. In some embodiments, at least two of the units may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or any combination thereof).

Pre-processing unit 302 may process different kinds of information received from acquisition module 131, control module 132, storage module 133, and/or display 135. The information may include the ECT data, basic information regarding a subject, a control parameter (e.g., acquisition frequency, acquisition rate, or the like), a display parameter (e.g., brightness, resolution, scale, or the like), or the like, or a combination thereof. Merely by way of example, pre-processing unit 302 may process the ECT data, for example, to remove or reduce noises.

Gating control unit 304 may determine a gating parameter (e.g., a gate number) to gate the ECT data for image reconstruction. In some embodiments, the ECT data may be 4D data. As used herein, 4D data may refer to a data form containing time domain data and three dimensional (3D) spatial data. In some embodiments, the 4D data or a corresponding ECT image reconstructed based on the 4D data may be expressed as $\lambda(j, t)$, where j refers to a voxel (or an index) in the ECT image, the voxel corresponds to a spatial point of the subject, and t refers to a time axis (or a time point on the time axis). As used herein, "gate" may refer to that the ECT data may be divided into a plurality of sections along the time axis t and one of the sections may be selected to be processed to generate an ECT image. As used herein, "gate number" may refer to the number of the plurality of sections. In some embodiments, the coordinates of the time axis t may correspond to the gate number. For example, for a gate number n, the coordinates of the time axis t may be $\{1, 2, 3, \ldots, n\}$.

In some embodiments, during the acquisition of the ECT data, motions of the subject (e.g., respiratory motion or cardiac movements of the heart) may be unavoidable which may lead to motion blur in the ECT image reconstructed based on the ECT data. In order to reduce the motion blur, gating control unit 304 may gate the ECT data according to a gate number (e.g., n) into a plurality of sections and select one of the sections to reconstruct an ECT image. In some embodiments, the gate number may both influence the motion blur and the noise of the ECT image. For example, for a spatial point whose motion amplitude is $A_0$ (it is supposed that $A_0 > \varepsilon$, where $\varepsilon$ is the intrinsic resolution of the imaging system), if the gate number is n, the motion blur of a voxel corresponding to the spatial point may be reduced to $A_0/n$, and the noise of the voxel may be increased by $\sqrt{n}$.

In some situations, for different spatial points of the subject, motion information (e.g., motion amplitude) may be different. For example, the motion amplitude by respiratory motion of a spatial point on the back of a subject may be approximately zero, while the motion amplitude by respiratory motion of a spatial point of the chest of the subject may be relatively high. Relative to an ECT image reconstructed based on a non-gating approach, motion blur or noise of an ECT image reconstructed based on a gating approach may be modified. For example, for the ECT data acquired from the chest of the subject, to reduce the possible motion blur of voxels corresponding to the chest in the ECT image, a gate number of the gating approach may be determined based on the motion amplitude of the chest. In the ECT image, the motion blur of the voxels corresponding to chest may be reduced, but the noise of the voxels corresponding the chest may be reduced. In this situation, if a same gate number is selected for the ECT data acquired from the back of the subject where the motion amplitude is approximately zero, the noise of the voxels corresponding to the back may be reduced.

In some embodiments, considering that the motion amplitudes of different spatial points of a subject may be different, gating control unit 304 may determine different gate numbers for different ECT data acquired from different spatial points of the subject that correspond to different voxels in the ECT image, i.e. the number of gates of a region are locally adaptive to local motion amplitude. As used herein, "locally adaptive gating" indicates that imaging data corresponding to various spatial points of a subject may be gated differently based on conditions of the spatial points. In some embodiments, gate numbers determined based on the locally adaptive gating may integers. In some embodiments, gate numbers determined based on the locally adaptive gating may non-integers (e.g., fractions, decimals, etc.). For instance, according to locally adaptive gating, the number of gates of the imaging data corresponding to a region of the subject may be determined based on, e.g., the motion amplitudes of the spatial points within the region. Imaging data corresponding to two regions of the subject whose spatial points undergo motion of different motion amplitudes may be gated differently. The gating number determined based on locally adaptive gating may be referred to as an effective gating number. An effective gating number may be an integer or a non-integer.

In some embodiments, gating control unit 304 may determine a motion curve indicative of the motion amplitudes of different spatial points of the subject and determine different gate numbers based on the motion curve. In some embodiments, while determining the plurality of gate numbers, gating control unit 304 may take noise, motion blur, and user input into consideration. In some embodiments, gating control unit 304 may determine the gate numbers according to the motion amplitudes of the spatial points of the subject. In some embodiments, gating control unit 304 may determine the gate numbers according to an intermediate image against which value differences among voxels corresponding to the spatial points of the subject may be determined. Merely by way of example, a value of a voxel may refer to a grey level of the voxel. In some embodiments, gating control unit 304 may determine a temporal spread function based on the gate numbers, and further reconstruction unit 306 may reconstruct an ECT image based on the temporal spread function.

Reconstruction unit 306 may generate an ECT image relating to an object (e.g., a subject, or a portion thereof) based on the ECT data and the gate numbers. "Object" and "subject" may be used interchangeably in the present disclosure. For example, reconstruction unit 306 may gate the ECT data based on the gate numbers and reconstruct the ECT image based on the gated ECT data. In some embodiments, reconstruction unit 306 may employ different kinds of image reconstruction techniques for the image reconstruction procedure. Exemplary image reconstruction techniques may include Fourier slice theorem, filtered back projection algorithm, fan-beam reconstruction, iterative reconstruction, or the like, or a combination thereof. In some embodiments, reconstruction unit 306 may include one or more sub-units (not shown). The sub-units may reconstruct images by employing different reconstruction techniques. In some embodiments, the reconstructed image may be stored in storage unit 308.

Storage unit 308 may store the ECT data processed by pre-processing unit 302, the ECT image reconstructed by reconstruction unit 306, and the gating parameters determined by gating control unit 304. In some embodiments, the storage format may include text, picture, audio, video, code, or the like, or a combination thereof. In some embodiments, one or more algorithms that may be used during the processing, the reconstruction, or the gating control process may be stored in storage unit 308. The algorithm may include a threshold segmentation algorithm, an iterative algorithm, an interpolation algorithm, a statistical algorithm, a smoothing filtering algorithm, or the like, or any combination thereof.

It should be noted that the above description of processing module 134 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the assembly and/or function of processing module 134 may be varied or changed. In some embodiments, one or more units in processing module 134 may include an independent storage block (not shown) respectively and storage unit 308 may be optional. In some embodiments, any two or more units may be integrated into an independent unit used to implement more than one functions. As another example, pre-processing unit 302 may be optional.

Figure 4:
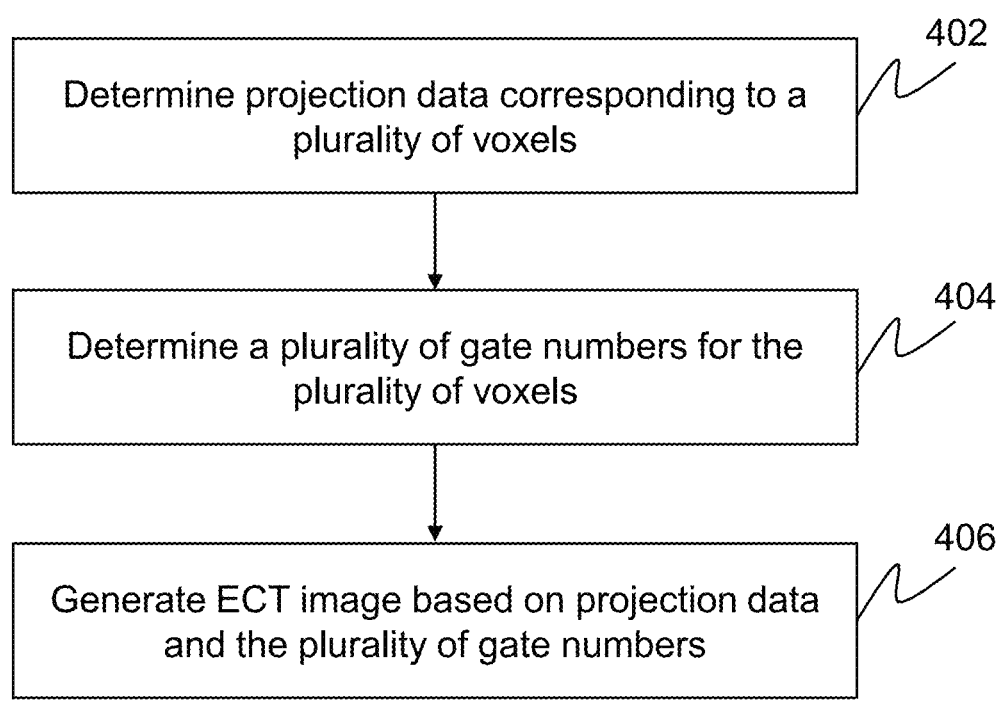
FIG. 4 is a flowchart illustrating an exemplary process for reconstructing an ECT image according to some embodiments of the present disclosure.

FIG. 4 is a flowchart illustrating an exemplary process for reconstructing an ECT image according to some embodiments of the present disclosure. In 402, processing module 134 may determine projection data corresponding to a plurality of voxels. In some embodiments, the projection data may be obtained by a single-bed whole-body PET scanner. The single-bed whole-body PET scanner may scan the subject to obtain projection data relating to a whole (total) body of a subject in a whole field of view (FOV). The whole field of view may cover the whole body of the subject. In some embodiments, the whole field of view may include a plurality of local volumes of interest (VOIs). A local VOI may cover a part or region of the subject. The plurality of voxels may correspond to a plurality of spatial points of a subject. In some embodiments, the projection data may be 4D data. As used herein, 4D data may refer to a data form containing time domain data and three dimensional (3D) spatial data. In some embodiments, processing module 134 may determine the projection data based on the ECT data acquired by acquisition module 110.

In 404, gating control unit 304 may determine a plurality of gate numbers for the plurality of voxels, where at least two of the plurality of gate numbers may differ from each other. The plurality of gate numbers may be associated with motion information of the plurality of voxels. In some embodiments, gating control unit 304 may determine the gate numbers according to the motion amplitudes of the spatial points of the subject corresponding to the plurality of voxels (e.g., a motion curve). For example, the motion amplitudes of the spatial points may be determined or obtained from a data library or a population-based distribution approach. Under the data library or the population-based distribution approach, the respiratory motion and/or cardiac movement of the heart may be considered similar among human beings. The motion amplitudes of the spatial points of a subject may be determined based on statistical data or clinical data. As another example, the motion amplitudes of the spatial points may be determined based on an image registration approach. Details about the image registration approach to determine the motion amplitudes may be found elsewhere in the present disclosure (e.g., in the description of FIG. 9).

Further, under the data library or the population-based distribution approach, the information of respiratory motion may be classified according to a criterion (e.g., age, gender, height, weight, or the like, or a combination thereof). The cardiac movement information of the heart may be handled similarly. Under the data library or the population-based distribution approach, the information of the cardiac movement of the heart may be classified according to a criterion (e.g., age, gender, height, weight, or the like). The motion amplitudes of the spatial points of a subject may be determined with an improved accuracy.

Merely by way of example, gating control unit 304 may determine the plurality of gate numbers by equation (1) below, that is, each of the plurality of gate numbers is a ratio of the motion amplitude of a spatial point corresponding to a voxel to the intrinsic resolution:

$$n(j)=A_0(j)/\varepsilon, \tag{1}$$

where j refers to the voxel index, $A_0(j)$ refers to the motion amplitude of a spatial point corresponding to voxel j, $\varepsilon$ refers to the intrinsic spatial resolution of the ECT system, and n(j) refers to the gate number for the voxel j.

In some embodiments, for different voxels, suitable gate numbers may be different under different situations. For example, if the ECT image is used for a noise-sensitive application, a suitable gate number for the voxel j may be less than $A_0(j)/c$. If the image is used for a quantitative-sensitive application, a suitable gate number for voxel j may be greater than $A_0(j)/c$. Therefore, the number of gates may be selected based on factors including, for example, desired image quality.

In some embodiments, gating control unit 304 may determine the plurality of gate numbers based on an intermediate image. In some embodiments, the ECT data acquired from different spatial points corresponding to different voxels in the intermediate image may be gated according to a uniform gate number and the intermediate image may be generated based on the gated ECT data. As used herein, the intermediate image may be a 4D image. Based on the intermediate image, a difference between a voxel in the intermediate image at a first time point and a corresponding voxel at a second time point may be determined. As used herein, corresponding voxels may refer to voxels at different time points that correspond to a same spatial point of a subject in the intermediate image. In some embodiments, a difference image may be determined based on the difference. Gating control unit 304 may determine a plurality of gate numbers for the plurality of voxels based on the difference image. For example, the larger the value (e.g., a grey level) of a specific voxel in the difference image is, the greater the gate number may be for the corresponding voxel.

In some embodiments, gating control unit 304 may further determine a feature relating to motion information of the plurality of voxels. For example, gating control unit 204 may determine a temporal spread function based on the plurality of locally adaptive number of gates, and the feature relating to the motion information may be a Full Width at Half Maximum of the temporal spread function. In some embodiments, the temporal spread function may refer to a blurring effect (e.g., a Gaussian blur). In some embodiments, the temporal spread function may relate to spatial information and time information of the ECT data (or the projection data) acquired from different spatial points of a subject.

In 406, reconstruction unit 306 may generate an ECT image based on the projection data and the plurality of gate numbers. In some embodiments, the pre-processing unit 302 may select the projection data. For example, the subject may have a voluntary motion and an involuntary motion during the scanning. The voluntary motion of the subject may refer to a motion that can be voluntarily controlled by the subject (e.g., a motion of the head, a leg, a foot, etc.). The involuntary motion may refer to a motion that cannot be voluntarily controlled by the subject (e.g., motions of a lung, the heart, etc.). If an amplitude of the voluntary motion exceeds a voluntary motion threshold during a time period, the projection data collected in the time period may be omitted in the image reconstruction. Details about the imaging data selection may be found elsewhere in the present disclosure (e.g., in the description of FIG. 10).

In some embodiments, the gating control unit 304 may determine a gating area for the subject in the whole (total) field of view. In some embodiments, the determination may be operated based on a scout image. The scout image may include an image reconstructed using one or more groups of the gated imaging data. For example, the scout image may be a fused image of the first gated image and the second gated image. In some embodiments, the determination may be based on the determined motion amplitudes of spatial points of the subject automatically or implemented in response to one or more gating instructions by the user. In some embodiments, the gating control unit 304 may determine different gate numbers for different parts of the subject. Each part of the subject may have a local gating number. For example, for each local VOI of the subject, the gating control unit 304 may determine a corresponding local gating number. For a single-bed whole-body PET scanner, the local gating numbers of various parts or regions of the subject may be determined based on the motion amplitudes independently. That is, the determination of the gating number of a part or region may be performed independently from the determination of the gating number of another part.

In some embodiments, the gating area may be determined automatically. For example, the processing module 134 may determine spatial points having an involuntary motion. Then the processing module 134 may determine the gating area including spatial points having the involuntary motion or whose motion amplitudes exceed an involuntary motion threshold.

In some embodiments, the gating area may be determined in response to the one or more gating instructions provided by the user. For example, the user may determine the gating area based on the motion amplitudes determined before, and give the gating instruction to the gating control unit 304 via a user interface (e.g., in the description of FIG. 11).

In some embodiments, gating control unit 304 or reconstruction unit 306 may gate the projection data based on the plurality of gate numbers. For example, for a specific voxel, gating control unit 304 or reconstruction unit 306 may gate the projection data acquired from a spatial point corresponding to the specific voxel along the time axis according to a corresponding gate number of the plurality of gate numbers; gated projection data may include the projection data for voxels and their respective gate numbers; reconstruction unit 306 may reconstruct an ECT image based on the gated projection data.

In some embodiments, the plurality of gating numbers may be assigned to the image data based on the motion amplitudes of spatial points corresponding to the image data. For instance, only image data corresponding to spatial points with a gating area are to be gated; a plurality of gating numbers are assigned to the image data within the gating area based on the motion amplitudes of the corresponding spatial points within the gating area.

In some embodiments, reconstruction unit 306 may reconstruct one or more gated ECT images based on the temporal spread function. In some embodiments, reconstruction unit 306 may generate the gated ECT images based on an image reconstruction algorithm. The image reconstruction algorithm may include Maximum Likelihood Expectation Maximization (MLEM) algorithm, Ordered Subset Expectation Maximization (OSEM) algorithm, Maximum Likelihood reconstruction of Attenuation and Activity (MLAA) algorithm, or the like, or a combination thereof.

Merely by way of example with reference to the reconstruction of gated PET images, the distribution of the projection data of the voxels may be approximated by a Poisson distribution, and a likelihood function of the distribution of the projection data may be described by equation (2):

$$\mathcal{L}(x,p)=\Pi_i(\hat{p}_i)^{p_i}(p_i!)^{-1}\exp(-\hat{p}_i) \quad (2)$$

where $\mathcal{L}(x, p)$ refers to the likelihood function of the distribution of the projection data, x refers to the distribution of the projection data p, i refers to the $i^{th}$ LOR of the projection data, and $\hat{p}_i$ refers to an estimation of the projection data of the $i^{th}$ LOR.

In some embodiments, the projection data may be estimated based on a projection matrix of the imaging system, an estimation of the distribution of the PET tracer within the subject, scattering events, or random events. As used herein, the projection matrix may be determined based on default settings of the imaging system, or provided by a user. The scattering events and random events may be determined based on statistical data or empirical data. For example, the estimation of the projection data may be determined by equation (3):

$$\hat{p}=HF+S+R, \quad (3)$$

where $\hat{p}$ refers to the estimation of the projection data, H refers to the projection matrix of the ECT system, F refers to a vector of an estimated PET image corresponding to an estimation of the distribution of the PET tracer within the subject (generally in an ECT process, F refers to an estimated ECT image), S refers to scattering events, and R refers to the random events.

In some embodiments, the estimated ECT images may be determined based on a first substituted ECT image by a first interpolation function. As used herein, the first substituted ECT image may refer to an ECT image corresponding to the distribution of the ECT tracer within the subject. For different voxels (or different spatial points of the subject) in the first substituted ECT image, the coordinates of the time axis may be different; that is, for different voxels, the lengths of the time axis may be different. For example, for voxel j, the coordinates of the time axis may be $\{1, 2, 3, \ldots, n(j)\}$, and the length of the time axis may be n(j), where n(j) is an integer.

For example, the estimated ECT image may be determined based on the first substituted ECT image by equation (4):

$$F(j,g)=\Sigma_{t=1}^{n(j)}u_j(g,t)\lambda(j,t), \quad (4)$$

where j refers to the voxel index, g and t refer to temporal indexes (also referred to as the "coordinates of the time axis"), F(j, g) refers to the estimated ECT image, λ(j, t) refers to the first substituted ECT image, and $u_j(g, t)$ refers to the first interpolation function.

In some embodiments, in the estimated ECT images determined based on the first substituted ECT image, for different voxels (or different spatial points of the subject), the coordinates of the time axis is uniform; that is, for different voxels, the lengths of the time axis is uniform (i.e., G, the maximum one of the plurality of gate numbers (also referred to as a "threshold relating to the plurality of gate numbers)). For example, for voxel j, the length of the time axis is G, and the gate number may be n(j), where n(j) may be an integer or not. Under actual operation, an integer is suitable for the value of n(j), while under theoretical case, a non-integer is suitable for the value of n(j).

In some embodiments, the first interpolation function may include a linear interpolation function, a cubic interpolation function, a spline interpolation function, or the like, or a combination thereof. For example, the first interpolation function may be expressed as equation (5):

$$u_j(g,t) = \begin{cases} 0, t \neq \lfloor \frac{g*n(j)}{G} \rfloor, & t \neq \lfloor \frac{g*n(j)}{G} \rfloor + 1 \\ \{ \frac{g*n(j)}{G} \}, & t = \lfloor \frac{g*n(j)}{G} \rfloor + 1, \\ 1 - \{ \frac{g*n(j)}{G} \}, & t = \lfloor \frac{g*n(j)}{G} \rfloor \end{cases} \quad (5)$$

where j refers to the voxel index, g and t refer to temporal indexes, n(j) refers to the gate number determined for the $j^{th}$ voxel (also referred to as the "length of the time axis"), G refers to the maximum gate number of the plurality of gate numbers, symbol $\lfloor x \rfloor$ refers to a function for determining a maximum integer which is less than or equal to x, and symbol $\{x\}$ refers to a function for determining a fractional part of x, that is, $\{x\}=x-\lfloor x \rfloor$.

In some embodiments, the first substituted ECT image may be determined based on a second substituted ECT image by a second interpolation function. For different voxels in the second substituted ECT image, the coordinates of the time axis may be uniform; that is, for different voxels, the lengths of the time axis may be uniform (G, the maximum one of the plurality of gate numbers). For voxel j, the length of the time axis is G, and the gate number may be n(j), where n(j) is an integer or not. For example, the first substituted ECT image may be determined by equation (6):

$$\lambda(j,t)=\Sigma_{\tau=1}^{G}(v_j(t,\tau)f(j,\tau)), \quad (6)$$

where j refers to the voxel index, τ and t refer to temporal indexes, G refers to the uniform length of the time axis (i.e., the maximum one of the plurality of gate numbers), Δ(j, t) refers to the first substituted ECT image, $v_j(t, \tau)$ refers to the second interpolation function, and $f(j, \tau)$ refers to the second substituted ECT image.

In some embodiments, considering that the first substituted ECT image may be determined by the second substituted ECT image, there may be a relationship between the estimated ECT image and the second substituted ECT image. For example, the estimated ECT image and the second substituted ECT image may be linked by a temporal spread function as expressed in equation (7):

$$F(j,g)=\Sigma_{\tau=1}^{G}w_j(g,\tau)f(j,\tau), \quad (7)$$

where j refers to the voxel index, g and τ refer to temporal indexes, G refers to the uniform length of the time axis (i.e., the maximum gate number of the plurality of gate numbers), F(j, g) refers to the estimated ECT image, $f(j, \tau)$ refers to the second substituted ECT image, and $w_j(g, \tau)$ refers to the temporal spread function.

In some embodiments, the temporal spread function may be determined by the first interpolation function. For example, the estimated ECT image may be determined by equation (8):

$$F(j,g) = \sum_{t=1}^{n(j)} \lambda(j,t) = \sum_{t=1}^{n(j)} u_j(g,t) \sum_{\tau=1}^{G} (v_j(t,\tau) f(j,\tau)) = \sum_{\tau=1}^{G} w_j(t,\tau) f(j,\tau), \quad (8)$$

where j refers to the voxel index, b, τ, and t refer to temporal indexes, G refers to the uniform length of the time axis (i.e., the maximum gate number of the plurality of gate numbers), F(j, g) refers to the estimated ECT image, λ(j, t) refers to the first substituted ECT image, $u_j(g, t)$ and $v_j(t, \tau)$ refer to the first interpolation function and the second interpolation function, respectively, $f(j, \tau)$ refers to the second substituted ECT image, and $w_j(g, \tau)$ refers to the temporal spread function.

Therefore, the temporal spread function may be determined by equation (9):

$$w_j(g,\tau) = \sum_{t=1}^{n(j)} u_j(g,t) v_j(t,\tau), \quad (9)$$

where j refers to the voxel index, g and t refer to temporal indexes, $u_j(g, t)$ and $v_j(t, \tau)$ refer to the first interpolating function and the second interpolating function, respectively, n(j) refers to the gate number determined for the $j^{th}$ voxel, and $w_j(g, \tau)$ refers to the temporal spread function. For voxel j, the gate number n(j) may not be an integer. For instance, the gate number n(j) may be a fraction or a decimal.

In some embodiments, the temporal spread function may be determined based on the plurality of gate numbers. In some embodiments, the temporal spread function may be determined by a blurring function (e.g., a Gaussian blurring function). In some embodiments, the Full Width at Half Maximum (FWHM) of the blurring function may equal to G/n(j). For example, the time spread function may be determined by equation (10):

$$w_j(g, \tau) = \frac{1}{c_g} \exp\left(-\ln(2) \frac{4(\tau - g)^2}{(G/n(j))^2}\right), \quad (10)$$

where j refers to the voxel index, g and τ refer to temporal indexes, G refers to the uniform length of the time axis (i.e., the maximum gate number of the plurality of gate numbers), n(j) refers to the gate number for the $h^{th}$ voxel, and $C_g$ refers to a constant value. $C_g$ may be determined by $\Sigma_\tau w_j(g, \tau) = 1$. As another example, the temporal spread function may be determined by equation (11):

$$w_j(g, \tau) = \begin{cases} 1, & \tau = g \\ 0, & \text{Otherwise} \end{cases}, \quad (11)$$

where j refers to the voxel index, and g and τ refer to temporal indexes.

In some embodiments, the first substituted ECT image may be determined by combining equation (3) and equation (4) with the MLEM algorithm. An iterative function for the first substituted ECT image may be determined by equation (12):

$$\lambda_{j,t}^{m+1} = \frac{\lambda_{j,t}^m}{\sum_g u_{j,g,t} \sum_i H_{i,j}} \sum_g u_{j,g,t} \sum_i \frac{H_{i,j} P_{i,g}}{\sum_k H_{i,k} \sum_\tau u_{k,g,t} \lambda_{k,t}^m + S_g + R_g}, \quad (12)$$

where j and k refer to voxel indexes, g, τ, and t refer to temporal indexes, m refers to the iterative index, u refers to the first interpolating function, H refers to the projection matrix of the ECT system, S refers to the scattering events, R refers to the random events, P refers to the projection data, and refers to the first substituted ECT image.

In some embodiments, the second substituted ECT image may be determined by combining equation (4) and equation (7) with the MLEM algorithm. An iterative function for the second substituted ECT image may be determined by equation (13):

$$f_{j,\tau}^{m+1} = \frac{f_{j,\tau}^m}{\sum_g w_{j,g,\tau} \sum_i H_{i,j}} \sum_g w_{j,g,\tau} \sum_i \frac{H_{i,j} P_{i,g}}{\sum_k H_{i,k} \sum_\tau w_{k,g,\tau} f_{k,\tau}^m + S_g + R_g}, \quad (13)$$

where j and k refer to voxel indexes, g, τ, and t refer to temporal indexes, m refers to the iterative index, w refers to the temporal spread function, H refers to the projection matrix of the ECT system, S refers to the scattering events, R refers to the random events, P refers to the projection data, and f refers to the second substituted ECT image.

In some embodiments, the iterative function may begin with a uniform distribution estimation. To identify a difference between the estimated projection data and the actually measured projection data, they may be compared during the iteration process. During the iterative process, the estimated projection data may be updated and a new iteration may be performed. The difference between the estimated projection data and the actually measured projection data may be reduced during the iterative process. In some embodiments, the iterative process may proceed until the difference between the estimated projection data and the actually measured projection data is less than a threshold value. In some embodiments, the iterative process may proceed until the difference between the estimated projection data and the actually measured projection data stables—the change of the differences between a certain number (e.g., 2, 3, 4) of consecutive iterations falls within a threshold value. In some embodiments, the iterative process may proceed until the number of iterations that have been performed exceeds a threshold value. The threshold value may be determined based on default settings of imaging system, or provided by a user.

In some embodiments, the estimated ECT image may be determined based on the first substituted ECT image or the second substituted ECT image. In some embodiments, image processing system 100 may generate an ECT image based on the estimated ECT image, the first substituted ECT image, and/or the second substitute ECT image.

FIG. 5-A is a flowchart illustrating an exemplary process for determining a plurality of gate numbers for a plurality of voxels according to some embodiments of the present disclosure. In 502, gating control unit 304 may generate an intermediate image based on the projection data corresponding to a plurality of voxels. For example, gating control unit 304 may gate the projection data according to a uniform gate number for the plurality of voxels.

In 504, gating control unit 304 may determine a difference between a voxel at a first time point and a corresponding voxel at a second time point based on the intermediate image. As used herein, corresponding voxels may refer to voxels at different time points that correspond to a same spatial point of a subject in one or more intermediate images corresponding to the one or more time points. For example, the difference may be determined by x(j, g)−x(j, t), where j refers to the voxel index, g and t refer to temporal indexes, x(j, t) refers to the value (e.g., a grey level) of the $j^{th}$ voxel at time point t, and x(j, g) refers to the value (e.g., a grey level) of the $j^{th}$ voxel at time point g.

In 506, gating control unit 304 may determine a difference image based on the difference determined in 504. For example, the difference image may be determined by equation (14):

$$D(j, t) = \sqrt{\sum_{g=1}^{G} (x(j, g) - x(j, t))^2} \bigg/ \sum_{g=1, g \neq t}^{G} x(j, g), \quad (14)$$

where j refers to the voxel index, g and t refer to temporal indexes, G refers to the uniform length of the time axis (i.e., the maximum one of the plurality of gate numbers), x(j, t) refers to the value of the $j^{th}$ voxel at time point t, x(j, g) refers to the value of the $j^{th}$ voxel at time point g, and D(j, t) refers to the difference image.

In 508, gating control unit 304 may determine a plurality of gate numbers for the plurality of voxels based on the difference image. For example, for the $j^{th}$ voxel, the larger the value of the voxel at time point t in the difference image is, the greater the gate number may be for the $j^{th}$ voxel. For example, the gate number for the $j^{th}$ voxel may be determined by equation (15):

$$n(j) = G * \frac{\max_{t}(D(j, t))}{\max_{t,j}(D(j, t))}, \quad (15)$$

where n(j) refers to the gate number for the $j^{th}$ voxel, G refers to the uniform length of the time axis (i.e., the maximum gate number of the plurality of gate numbers), and D(j, t) refers to the value of the $j^{th}$ voxel at time point t in the difference image.

After the plurality of gate numbers are determined, gating control unit 304 may further determine the temporal spread function according to equation (10).

Figure 6:
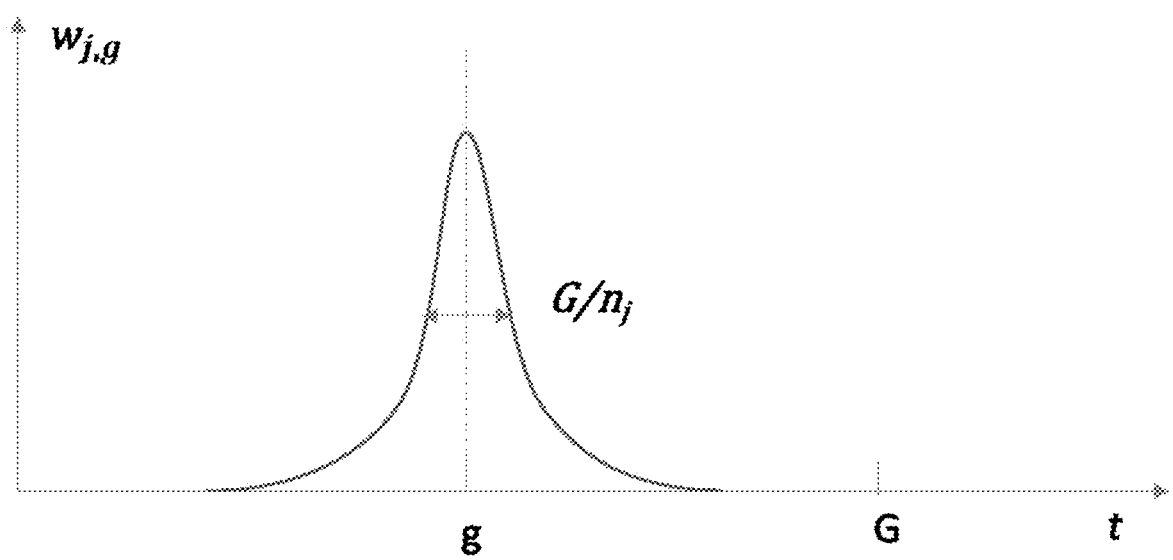
FIG. 6 is a schematic diagram illustrating an exemplary temporal spread function according to some embodiments of the present disclosure.

In some embodiments, the temporal spread function illustrated in FIG. 6 may be determined based on the difference image. For example, the larger the value of the $j^{th}$ voxel at time point t in the difference image is, the lower the value of the FWHM of the temporal spread function may be.

FIG. 5-B1 through FIG. 5-B3 are diagrams illustrating exemplary gating approaches based on motion amplitudes according to some embodiments of the present disclosure. In the three diagrams, the horizontal axis represent spatial coordinates. The spatial points of the subject corresponding to the voxels in reconstructed images may distribute along the spatial coordinates. The solid-line vertical axis represents effective gate numbers. The dashed-line vertical axis represents motion amplitudes. A solid line represents a distribution of the effective gate numbers at various spatial points. A dashed line represents a distribution of the motion amplitudes corresponding to various spatial points. The distribution of motion amplitudes may be obtained using, for example, the methods disclosed in the present disclosure.

FIG. 5-B1 illustrates a conventional gating approach. For the spatial points, the corresponding effective gate numbers may be determined as a constant value despite various motion amplitudes of the spatial points.

FIG. 5-B2 illustrates a locally adaptive gating approach with an integer gating number. The effective gate numbers may be determined based on the motion amplitudes. As shown in the figure, a higher motion amplitude may correspond to a larger effective gate number. Various motion amplitudes within a range may correspond to a same effective gate number. An effective gate number is an integer. Details about the locally adaptive gating may be found elsewhere in the present disclosure (e.g., in the description of FIG. 4).

FIG. 5-B3 illustrates a locally adaptive gating approach with a non-integer gating number determined based on temporal spread functions of the spatial points. A gating number so determined may be a non-integer. Compared to the solid step-curve illustrated in FIG. 5-B2, the solid continuous curve illustrated in FIG. 5-B3 follows the curve of the motion amplitudes more accurately.

FIG. 6 is a schematic diagram illustrating an exemplary temporal spread function according to some embodiments of the present disclosure. As illustrate in FIG. 6, the curve may donate an exemplary temporal spread function for the $j^{th}$ voxel varying with time t. The FWHM of the curve equals to G/n(j). The greater the value of the FWHM is, the smoother the curve of the temporal function may be. In some embodiments, the value of the FWHM may be determined based on the motion amplitude of the spatial point of the subject corresponding to a voxel. For example, the value of the FHWM may be determined based on the difference image described with reference to FIG. 5-A. In some embodiments, the FWHM may be determined by G/n(j), where G refers to the uniform length of the time axis (i.e., the maximum gate number of the plurality of gate numbers), and n(j) refers to the gate number for the $j^{th}$ voxel.

Figure 9:
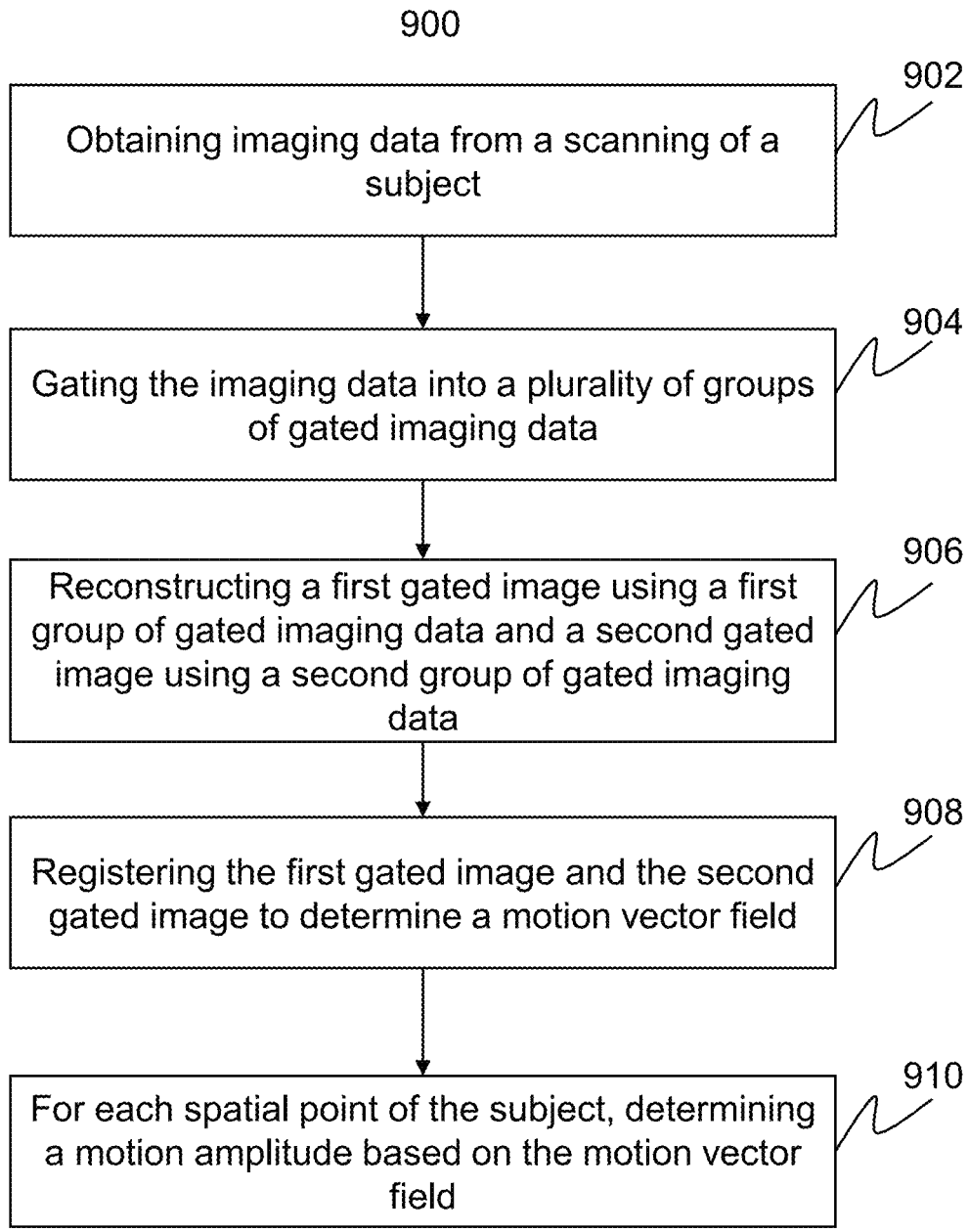
FIG. 9 is a flowchart illustrating an exemplary process for determining motion amplitudes of spatial points of a subject according to some embodiments of the present disclosure.

FIG. 9 is a flowchart illustrating an exemplary process 900 for determining motion amplitudes of spatial points of a subject according to some embodiments of the present disclosure. In some embodiments, the process 900 may be applied in connection with the ECT imaging techniques.

In 902, the processing module 134 may obtain imaging data from a scanning of a subject. In some embodiments, the scanning may include an ECT scanning. The imaging data may include the projection data described elsewhere in the present disclosure. See, for example, relevant description with reference to FIG. 4. In some embodiments, the projection data may include PET projection data, sonogram data, list mode data, etc. Merely by way of example, the imaging data may be 4D data and stored in a list mode. For example, the imaging data may be arranged based on the time axis.

In 904, the gating control unit 304 may gate (or referred to as divide) the imaging data into a plurality of groups (or referred to as frames) of gated imaging data. The gating numbers may be any positive number. In some embodiments, the gating numbers may be determined empirically for a subject. Each of the groups of gated imaging data may be used to reconstruct an image. In some embodiments, the processing module 134 may number the groups. Different groups may correspond to different time periods of a motion (e.g., a voluntary motion, an involuntary motion, or both).

For example, different groups may correspond to different time periods of a respiratory motion; group 1 may correspond to an end period of inspiration motion (also referred as end inspiration phase); group N may correspond to an end period of expiration motion (also referred as end-expiration phase); a group between group 1 and group N, e.g., group 2, . . . , group (N−1), may correspond to a period between the end period of inspiration motion and the end period of expiration motion. Similarly, in a cardiac motion, a group may correspond to an end-diastolic phase, and a different group may correspond to an end-systolic phase. As another example, different groups may correspond to different time periods of a voluntary motion; group 1 may correspond to a starting period of a head motion of the subject; group N may correspond to an end period of the head motion; a group between group 1 and group N, e.g., group 2, . . . , group (N–1), may correspond to a period between the starting period and the end period of the head motion. In some embodiments, different groups may correspond to different time periods of a voluntary motion and concurrently an involuntary motion.

In 906, the reconstruction unit 306 may reconstruct a first gated image using the first group of gated imaging data and a second gated image using the second group of gated imaging data. The first gated image and second gated image may also be referred to as intermediate images. As used herein, an intermediate image may refer to one reconstructed based on gated raw imaging data. The first group of gated imaging data or the first gated image may correspond to the same spatial points in the scanning of the subject.

In some embodiments, the first group of gated imaging data and the second group of gated imaging data may correspond to characteristic periods of the respiratory motion of a subject. For example, the first group of gated imaging data and the second group of gated imaging data may correspond to the end period of an inspiration motion and the end period of an expiration motion of the respiratory motion, respectively. The motion amplitude of a spatial point corresponding to the two characteristic periods may be maximum within a cycle of the respiratory motion of the subject.

Merely by way of example, the imaging data may be the PET projection data. The reconstruction of the PET image may be performed based on an OS-EM algorithm. There may be attenuation of the projection data because of loss of detection of true coincidence events. When the photons pass through the tissue to reach the detector 112 (e.g., a PET detector), part of the positive electrons may reach the detector 112, and the rest of the photons may be scattered or absorbed by the tissue of the patient. And the photons scattered or absorbed may cause the attenuation of the photon ray which in turn may contribute to the attenuation artifacts in the PET image. In the PET/CT system, x-rays from a CT scan may be used to construct an attenuation map throughout the body, or a portion thereof. The attenuation map may be used to correct the attenuation in the PET data. Attenuation-mismatch artifacts may be present due to continuous respiration during both the PET and CT scans. Attenuation-mismatch artifacts may appear when the CT scan whose data are used to construct the attenuation map corresponds to a different motion phase than the PET scan whose data are used to produce a PET image based on the attenuation map. In some embodiments, the attenuation map used in the reconstruction algorithm may be modified by filling a region of the attenuation map that corresponds to a portion (e.g., the lung, the heart) of the subject having a relatively large motion with the attenuation coefficient of a soft tissue to avoid or reduce the attenuation-mismatch artifacts.

In some embodiments, the reconstructed image may be 2D images in a coronal plane and a sagittal plane. In some embodiments, the reconstructed image may be 3D images. It is understood that 2D images in the coronal plane and in the sagittal plane are mentioned for illustration purposes and not intended to limit the scope of the present disclosure. For a specific motion type, images in one or more planes describing the motion may be used. The 3D image may include a coronal view image, a sagittal view image, a transverse view image, or a view at an oblique angle. In some embodiments, the motion vectors in coronal and sagittal planes may be used to determine the motion amplitudes. In some embodiments, the motion vectors in the coronal and sagittal planes may be determined based on 2D maximum intensity projection (MIP) images in the coronal view and in the sagittal view generated from a 3D reconstructed image.

In 908, the processing module 134 may register the first gated image and the second gated image to determine the motion vector field. The first gated image and second gated image may be 2D images or 3D images. The motion vector field may be a 2D motion vector field or a 3D motion vector field. For instance, 2D images corresponding to two motion phases of a motion type may be subject to 2D registration to obtain a 2D motion vector field in the coronal plane and a 2D motion vector field in the sagittal plane. The 2D motion vector field in the coronal plane and the 2D motion vector field in the sagittal plane may be used to compose a 3D motion vector field including a plurality of 3D motion vectors. As another example, 3D images may be subject to 3D registration to provide a 3D motion vector field. Various registration algorithms may be used. For instance, both rigid registration and non-rigid registration may be performed.

The motion vector field may include the plurality of motion vectors. The plurality of motion vectors may be 3D vectors. Each of the motion vectors may indicate a motion of a spatial point between different motion phases as represented in the first gated image and the second gated image.

For instance, the registration algorithm may include a B-spline image registration algorithm. An exemplary cost function of the B-spline registration is:

$$E(m) = D(I, T(J, m)) + \alpha \|\Delta m\|^2, \quad (16)$$

where $D(I, T(J, m))$ refers to a difference between the images I and J, I and J refers to the two images to be registered, m refers to the motion vector field, $T(J, m)$ refers to image J transformed using the motion vector field m, $\alpha$ is a positive scalar for the smoothing term $\|\Delta m\|^2$; and $\Delta$ is the Laplace operator. The difference between two images may be assessed in terms of a parameter such as, for example, the grey values of pixels/voxels in images, or the intensity distribution patterns in the images, etc. $D(I, T(J, m))$ may be in the form of the sum of squared differences (SSD), the sum of absolute difference (SAD), mutual information (MI), etc., with respect to the parameter. The processing module 134 may further determine the first motion vector and the second motion vector for each of the spatial points (e.g., the vector $m_c$ and vector $m_s$ in equation (18)) based on the motion vector field m. $D(I, T(J, m))$ may be determined by equation (17):

$$D(I, T(J, m)) = \Sigma_i (I(x_i) - J(x_i + m(x_i)))^2, \quad (17)$$

where $I(x_i)$ refers to reference image, $m(x_i)$ refers to motion vector field from J to I, $J(x_i + m(x_i))$ refers to transformed image J using motion vector field m, $x_i$ refers to coordinate of voxel i, and i refers to voxel index in image space.

In 910, for each spatial point, the processing module 134 may determine a motion amplitude based on the motion vector field. In some embodiments, the motion amplitude of a spatial point may be determined based on the first motion vector and the second motion vector. In some embodiments, the motion amplitudes may be determined by equation (18):

$$A_0(j) = \sqrt{\|m_c(j)\| \cdot \|m_s(j)\|} \, A_e(j), \qquad (18)$$

where j refers to the voxel index, $A_0(j)$ refers to the motion amplitude of a spatial point corresponding to voxel j, $m_c(j)$ refers to the 2D motion vector in the coronal plane, $m_s(j)$ refers to the 2D motion vector in the sagittal plane, and $A_e(j)$ refers to an predetermined motion amplitude. In some embodiments, the predetermined motion amplitude $A_e(j)$ may be determined by the user based on prior experience. The value range of the $A_e(j)$ is 0 to 1. Merely by way of example, based on empirical information, the amplitude for the respiratory motion of a human subject is: $A_e(j)$ for the head is 0, $A_e(j)$ for the chest is 1, and $A_e(j)$ for the lower body part is 0.

Figure 10:
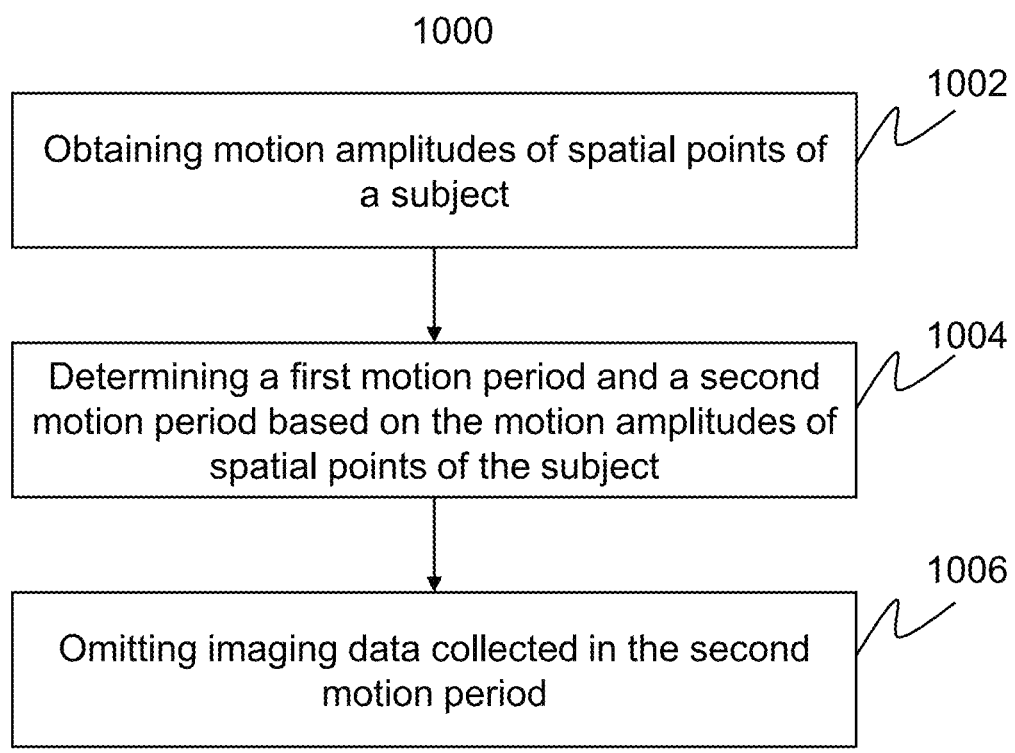
FIG. 10 is a flowchart illustrating an exemplary process for selecting the imaging data according to some embodiments of the present disclosure.

FIG. 10 is a flowchart illustrating an exemplary process 1000 for selecting the imaging data according to some embodiments of the present disclosure. In some embodiments, the process 1000 may include omitting a portion of the imaging data before using the imaging data to reconstruct an image.

In 1002, the processing module 134 may obtain motion amplitudes of spatial points of a subject. In some embodiments, the motion amplitudes may be determined according to the process 900. In some embodiments, the motion amplitudes may be determined using an external device. For example, an external device including a plurality of sensors may be used to monitor the respiratory motion of the subject. The external device may generate a motion curve indicating the subject's movement during a scanning.

In 1004, the processing module 134 may determine a first motion period and a second motion period based on the motion amplitudes of spatial points of the subject. In some embodiments, the first motion period may refer to a time period when the subject has the involuntary motion, while the second motion period may refer to a time period when the subject has the voluntary motion. If the subject has a voluntary motion or the amplitude of a voluntary motion exceeds a threshold for a period, the imaging data collected during the period (e.g., a first motion period between a first motion phase and a second motion phase) may be omitted in image reconstruction to avoid or reduce motion artifact.

In some embodiments, the first motion period and the second motion period may be determined based on the motion curve determined by the external device. For example, the motion curve recording the amplitude of motions of the subject's head for a time period. During a portion of the time period, the amplitude of motions of the subject's head exceeds a predetermined threshold. The portion of the time period may be determined as the second motion period, while the other portion of the time period may be determined as the first motion period.

In some embodiments, the first motion period and the second motion period may be determined based on the motion amplitudes determined in process 900. For example, the imaging data may be collected during several respiratory cycles. For each cycle, the processing module 134 may determine motion amplitudes of the spatial points of the subject. If the motion amplitudes of spatial points corresponding to a portion of the subject (e.g., the head, the feet, etc.) exceeds a voluntary motion threshold, the subject may be considered to have a voluntary motion or the amplitude of the voluntary motion exceeds the voluntary motion threshold during the corresponding respiratory cycle. A respiratory cycle with the voluntary motion or a time period from the end period of inspiration to the end period of expiration may be determined as the second motion period.

In 1006, the processing module 134 may omit imaging data collected in the second motion period. As described before, the imaging data collected in the second period may include voluntary motion data that may cause motion artifact in the image reconstruction. The imaging data collected in the first motion period may be further used in image reconstruction.

Figure 12:
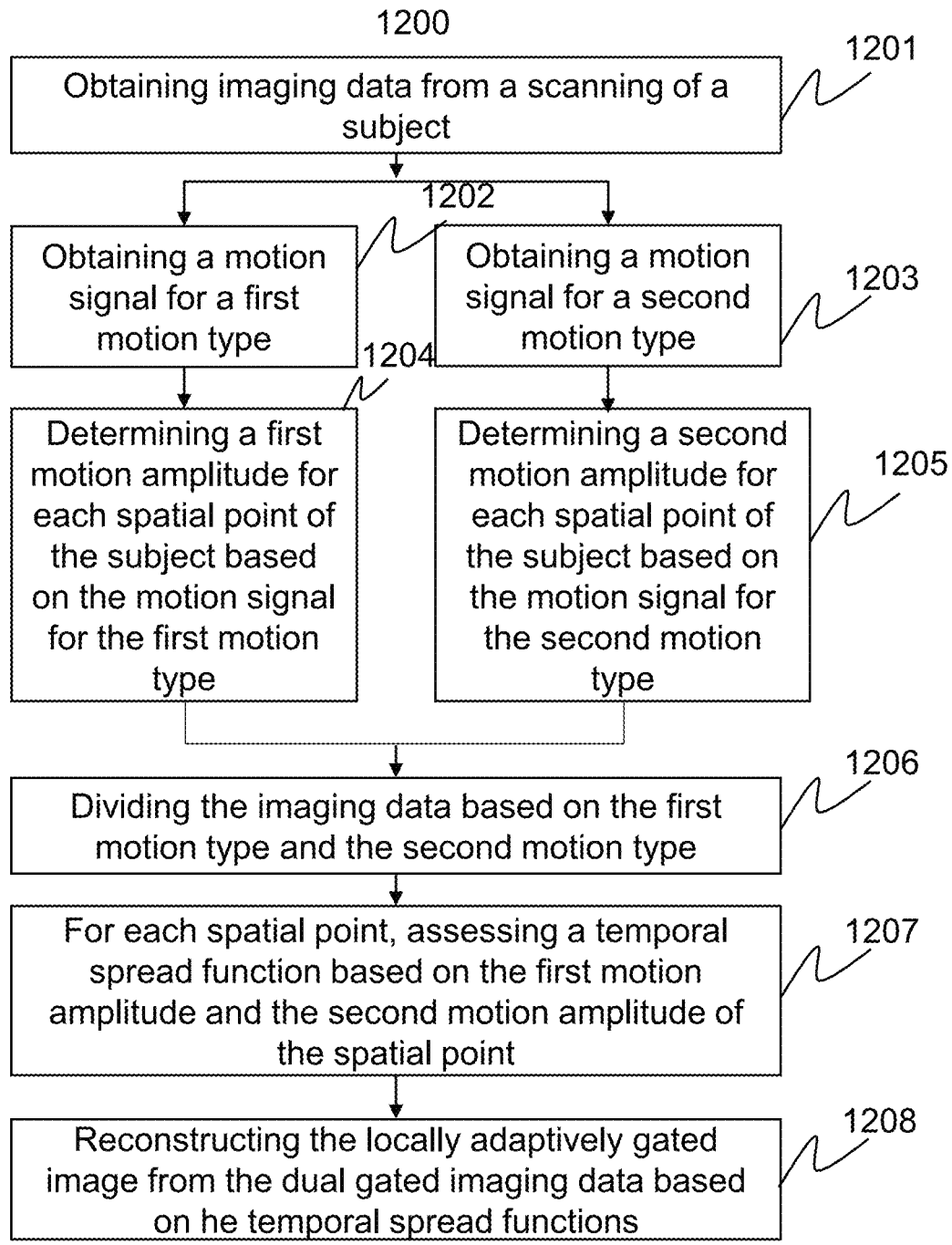
FIG. 12 is a flowchart illustrating an exemplary process for reconstructing a dual gated image according to some embodiments of the present disclosure.

FIG. 12 is a flowchart illustrating an exemplary process 1200 for reconstructing a dual gated image according to some embodiments of the present disclosure.

In 1201, the processing module 134 may retrieve imaging data from a scanning of a subject, similar to the description in 902. The data may be retrieved from the acquisition module 131 or a storage device (e.g., the storage module 133, the storage unit 308, etc.).

In 1202, the processing module 134 may obtain a first motion signal of a first motion type. In some embodiments, the first motion signal may include motion information of the motion amplitudes, time, etc. of the first motion type of the spatial points of the subject. The first motion type may include a type of voluntary motion as disclosed elsewhere in the present disclosure. In some embodiments, a first motion signal of the first motion type may be obtained from a motion sensor used to collect the motion information.

In 1203, the processing module 134 may obtain a second motion signal of a second motion type. The second motion signal may include motion information the motion amplitudes, time, etc., of the second motion type of the spatial points of the subject. The second motion type may include a type of involuntary motion. Exemplary involuntary motion includes respiratory motion, cardiac motion, etc. In some embodiments, a second motion signal of the second motion type may be obtained using a sensor including, e.g., a sensor to measure the cardiac activities of a subject, a sensor to measure respiratory activities of subject, etc.

In 1204, the processing module 134 (e.g., the gating control unit 304 of the processing module 134) may determine first motion amplitudes of the first motion type for spatial points of the subject based on the first motion signal of the first motion type. In some embodiments, the determination may be implemented according to the process 900. For example, the processing module 134 may dividing the imaging data into groups of the first gated imaging data based on the first motion signal. A group of the first gated imaging data may correspond to a motion phase of the first motion type of the subject. For example, a first group of the first gated imaging data may correspond to a first motion phase of the first motion type. A second group of the first gated imaging data may correspond to a second motion phase of the first motion type.

The reconstruction unit 306 may reconstructing a first gated image corresponding to the first motion phase of the first motion type using the first group of first gated imaging data and a second gated image corresponding to the second motion phase of the first motion type using the second group of first gated imaging data. In some embodiments, the reconstruction may be performed in a manner similar to the operations described in connection with 906.

The processing module 134 (e.g., the gating control unit 304 of the processing module 134) may register the first gated image and the second gated image to determine a motion vector field of the first motion type. The motion vector field of the first motion type may include a plurality of motion vectors of the first motion type. A motion vector of the first motion type may indicate a motion of the first motion type of a spatial point from the first motion phase to the second motion phase. The registration may be performed in a manner similar to the operations described in connection with 908.

The processing module 134 (e.g., the gating control unit 304 of the processing module 134) may determine a first motion amplitude of the first motion type for each spatial point based on the motion vector field of the first motion type (e.g., based on the motion vector of the first motion type corresponding to a spatial point). The determination may be performed in a manner similar to the operations described in connection with 910.

In 1205, the processing module 134 (e.g., the gating control unit 304 of the processing module 134) may determine second motion amplitudes of the second motion type for spatial points of the subject based on the motion signal of the second motion type. The determination may be implemented according to the process 900. For example, the processing module 134 (e.g., the gating control unit 304 of the processing module 134) may dividing the imaging data based on the second motion signal. A group of the second gated imaging data may correspond to a motion phase of the second motion type of the subject. For example, a first group of the second gated imaging data may correspond to the end-inspiration phase of a respiratory motion. A second group of the second gated imaging data may correspond to the end-expiration phase of the respiratory motion. As another example, a first group of the second gated imaging data may correspond to the end-diastolic phase of a cardiac motion. A second group of the second gated imaging data may correspond to the end-systolic phase of the cardiac motion.

The processing module 134 may execute similar operations in 1204, including the reconstructing, registering, and motion amplitude determination, with respect to the imaging data based on the second motion signal to obtain second motion amplitudes of the second motion type of the spatial points.

The reconstruction unit 306 may reconstructing a first gated image corresponding to the first motion phase of the second motion type using the first group of second gated imaging data and a second gated image corresponding to the second motion phase of the second motion type using the second group of second gated imaging data. In some embodiments, the reconstruction may be performed in a manner similar to the operations described in connection with 906.

The processing module 134 (e.g., the gating control unit 304 of the processing module 134) may register the first gated image and the second gated image to determine a motion vector field of the second motion type. The motion vector field of the second motion type may include a plurality of motion vectors of the second motion type. A motion vector of the second motion type may indicate a motion of a spatial point from the first motion phase to the second motion phase. The registration may be performed in a manner similar to the operations described in connection with 908.

The processing module 134 (e.g., the gating control unit 304 of the processing module 134) may determine a first motion amplitude of the second motion type for each spatial point based on the corresponding motion vector field of the second motion type of the first motion type (e.g., based on the motion vector of the second motion type corresponding to a spatial point). The determination may be performed in a manner similar to the operations described in connection with 910.

In 1206, the processing module 134 (e.g., the gating control unit 304 of the processing module 134) may divide or gate the imaging data based on dual gating of the first motion type and the second motion type. The dual gating may be based on a first gating based on the motion amplitudes of spatial points of the first motion type and a second gating based on the motion amplitudes of spatial points of the second motion type. The first gating or the second gating, or both, may be performed based on a locally adaptive gating approach.

Under the first gating based on the motion amplitudes of spatial points of the first motion type, the imaging data are to be divided into M frames; under the second gating based on the motion amplitudes of spatial points of a second motion type, the imaging data are to be divided into N frames. Under the dual gating, the imaging data are divided to M×N frames.

For instance, from a period starting at 0, imaging data may be divided under the first gating into 5 frames, such that the imaging data corresponding to a sub-period between 0-2 minutes belong to frame 1, imaging data corresponding to a sub-period between 2 minutes to 5 minutes belong to frame 2, . . . , and a sub-period between 8 minutes and 10 minutes belong to frame 5. From a period starting at 0, imaging data may be divided under the second gating into 10 frames, such that the imaging data corresponding to a sub-period between 0 and 0.5 minutes belong to frame 1, and imaging data corresponding to a sub-period between 0.5 minutes and 1 minutes belong to frame 2, . . . , and a sub-period between 9.5 minutes and 10 minutes belong to frame 10. Under the dual gating, the imaging data are divided into 50 frames. The lengths of the sub-periods may be the same or different.

The imaging data within a frame corresponding to a spatial point may be associated with a combined motion amplitude relating to both the first motion type and the second motion type. For a spatial point, the combined motion amplitude may be determined based on the first motion amplitude and the second motion amplitude of the spatial point. The first motion type or the second motion type may be a voluntary motion or an involuntary motion. An involuntary motion may include, e.g., respiratory motion, cardiac motion, etc.

In 1207, for each spatial point, the processing module 134 (e.g., the gating control unit 304 of the processing module 134) may assess a temporal spread function based on the combined motion amplitude of the spatial point. In some embodiments, the temporal spread function of a spatial point may be assessed further based on a first resolution recovery of the first motion type, and a second resolution recovery of the second motion type, in addition to the combined motion amplitude. For instance, the temporal spread function of a spatial point may be determined according to any one of equations (9)-(11) described elsewhere in the present disclosure. A resolution recovery, e.g. the first resolution recovery, the second resolution recovery, etc., may be determined based on the intrinsic system resolution. It may also be defined by a user. For instance, a user may specify a desired target resolution which may be larger than the intrinsic system resolution. A resolution recovery is larger than or equal to the intrinsic system resolution.

In 1208, the reconstruction unit 306 may reconstruct a dual gated image from the imaging data gated based on dual locally adaptive gating and the temporal spread functions. For instance, the image reconstruction may be performed according to equation (7) described elsewhere in the present disclosure.

In some embodiments, the processing module 134 (e.g., the gating control unit 304 of the processing module 134) may determine an intra-frame motion amplitude based on an intrinsic system resolution, which in turn depends on the material of the detector 112. As used herein, an intra-frame motion amplitude may refer to the residue motion after motion. The intra-frame motion amplitude determines the motion blurring effects. When the intra-frame motion amplitude is smaller than that of the intrinsic system resolution, no significant motion blurring would occur. For instance, the processing module 134 may further determine the number of gate corresponding to the second motion signal according to locally adaptive gating based on the intra-frame motion amplitude.

Figure 11:
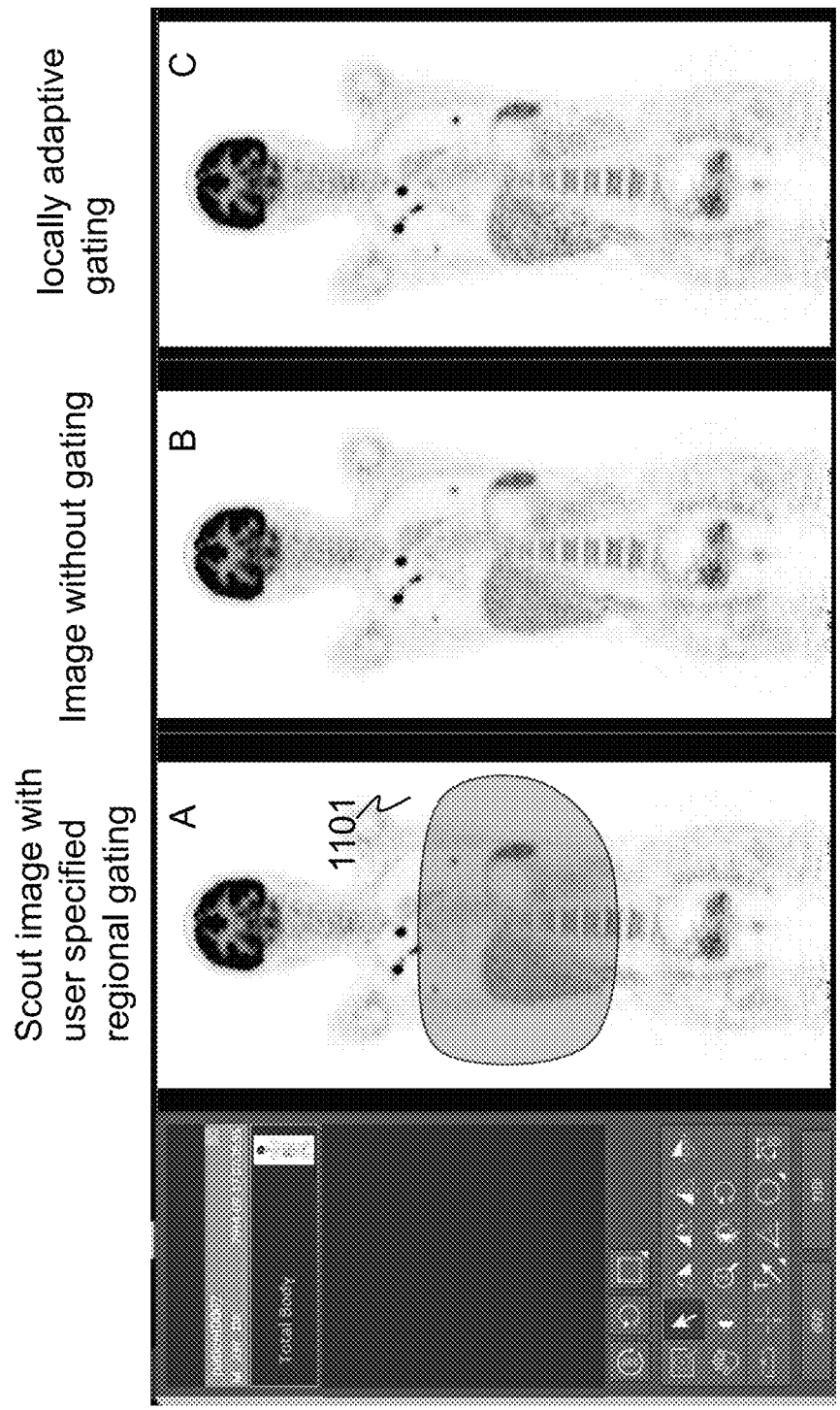
FIG. 11 illustrates an exemplary user interface for manually selecting gating area according to some embodiments of the present disclosure.

In some embodiments, the processing module 134 (e.g., the gating control unit 304 of the processing module 134) may further determine a gating area. In some embodiments, to perform the first gating, a first gating area may be selected. Similarly, to perform the second gating, a second gating area may be selected. The selection of the first gating area may be performed independently from the selection of the second gating area. The selection of the first gating area and/or the second gating area may be performed based on a user input (e.g., as illustrated in FIG. 11), or by the system 100. For instance, the selection of the first gating area and/or the second gating area may be performed by the system 100 based on the comparison between the motion amplitudes of spatial points of the voluntary motion with a threshold.

Merely by way of example, the processing module 134 may compare second motion amplitudes of the second motion type of the spatial points with a threshold that relates to a system intrinsic resolution. The processing module 134 may determine the gating area based on the comparison.

EXAMPLES

The following examples are provided for illustration purposes, and not intended to limit the scope of the present disclosure.

Example 1

FIG. 7-A, FIG. 7-B, and FIG. 7-C illustrate exemplary ECT images regarding a portion of a patient generated by different reconstruction approaches according to some embodiments of the present disclosure. For illustration purposes, 2D images are shown. The ECT image illustrated in FIG. 7-A was reconstructed based on the projection data that was processed based on the temporal spread function described in this disclosure. The ECT image illustrated in FIG. 7-B was reconstructed based on a non-gating approach (e.g., a point spread function approach). The ECT image illustrated in FIG. 7-C was reconstructed based on the projection data that was gated according to a uniform gate number.

It may be seen that the ECT image in FIG. 7-B has a low noise level but poor image resolution. The ECT image in FIG. 7-C has a high image resolution but high noise level. The ECT image in FIG. 7-A has a high noise level and a high image resolution. The noise level of the ECT image illustrated in FIG. 7-A is similar to that in FIG. 7-B. The image resolution of the ECT image illustrated in FIG. 7-A is similar to that in FIG. 7-C.

Example 2

FIG. 8-A, FIG. 8-B, and FIG. 8-C illustrate exemplary ECT images regarding phantom generated by different reconstruction approaches according to some embodiments of the present disclosure. For illustration purposes, 2D images are shown. The ECT image illustrated in FIG. 8-A was reconstructed based on the projection data that was processed based on the temporal spread function described in this disclosure. The ECT image illustrated in FIG. 8-B was reconstructed based on a non-gating approach (e.g., a point spread function method). The ECT image illustrated in FIG. 8-C was reconstructed based on the projection data that was gated according to a uniform gate number. It may be seen that the ECT image in FIG. 8-B has a low noise level but poor image resolution. The ECT image in FIG. 8-C has a high image resolution but high noise level. The ECT image in FIG. 8-A has a low noise level and a high image resolution. The noise level of the ECT image illustrated in FIG. 8-A is similar to that in FIG. 8-B. The image resolution of the ECT image illustrated in FIG. 8-A is similar to that in FIG. 8-C.

Example 3

FIG. 11 illustrates an exemplary user interface for manually selecting a gating area according to some embodiments of the present disclosure. As shown in the figure, three reconstructed images were arranged on the user interface. The image A is an image obtained through a scout reconstruction to provide a scout image. A gating area was determined based on an instruction provided by a user via a user interface, and the corresponding imaging data within the gating area were gated and applied in image reconstruction to generate image C. The image B is an image reconstructed without a gating approach. The image C is an image with a locally adaptive gating approach. According to the locally adaptive gating approach, a spatially variant gating number was applied locally to the imaging data for reconstruction. In the image A, a circle 1101 was determined by a user using the tools (the icons on the user interface) on the user interface. For example, an area selection tool may be used to select a circular area on the image of the subject to determine an area to be gated. The imaging data corresponding to spatial points included in the circle were gated during the reconstruction. Other exemplary icons may include an icon for rotating an image, an icon for generating a symmetric image, icons for zoom in/out, an icon for adjusting brightness, an icon for adjusting contrast, or the like, or a combination thereof.

It may be seen that image C in FIG. 11 has a high image resolution than that of the image B in FIG. 11.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for image processing implemented on at least one machine each of which has at least one processor and at least one storage device, the method comprising:
   a) obtaining imaging data acquired from a scanning of a subject;

b) obtaining a first motion signal of a first motion type;
c) obtaining a second motion signal of a second motion type;
d) dividing, based on the first motion signal, the imaging data into a plurality of groups of first gated imaging data, wherein a group of the first gated imaging data corresponds to a respective motion phase of the first motion type of the subject, a first group of the first gated imaging data corresponding to a first motion phase of the first motion type of spatial points of the subject, and a second group of the first gated imaging data corresponding to a second motion phase of the first motion type of the spatial points of the subject;
e) reconstructing a first gated image corresponding to the first motion phase of the first motion type using the first group of the first gated imaging data and a second gated image corresponding to the second motion phase of the first motion type using the second group of the first gated imaging data;
f) determining a motion vector field of the first motion type by registering the first gated image and the second gated image, wherein the motion vector field of the first motion type includes a plurality of motion vectors of the first motion type, a motion vector of the first motion type indicating a motion of a respective spatial point of the first motion type from the first motion phase to the second motion phase;
g) dividing, based on the second motion signal, the imaging data into a plurality of groups of second gated imaging data, wherein a group of the second gated imaging data corresponds to a respective motion phase of the second motion type of the subject, a first group of the second gated imaging data corresponding to a first motion phase of the second motion type of the spatial points of the subject, and a second group of the second gated imaging data corresponding to a second motion phase of the second motion type of the spatial points of the subject;
h) obtaining a motion vector field of the second motion type by performing e) and f) with respect to the imaging data divided based on the second motion signal;
i) dual gating, based on the first motion signal and the second motion signal, the imaging data;
j) for each of the spatial points, assessing a temporal spread function based on the motion vector of the first motion type and the motion vector of the second motion type of the spatial point; and
k) reconstructing an image from the dual gated imaging data and the temporal spread functions.

2. The method of claim 1, wherein the first motion type corresponds to a voluntary motion, and the second motion type corresponds to an involuntary motion.

3. The method of claim 1, wherein the determining the motion vector field of the first motion type by registering the first gated image and the second gated image includes:
performing a 2D image registration of the first gated image and the second gated image;
determining, for each of the spatial points, a 2D motion vector in a coronal plane and a 2D motion vector in a sagittal plane based on the registration; and
determining the motion vector field based on 2D motion vectors corresponding to the spatial points in the coronal plane and 2D motion vectors corresponding to the spatial points in the sagittal plane, wherein the motion vector field is three-dimensional.

4. The method of claim 1, wherein the registering the first gated image and the second gated image includes performing a 3D image registration, the method further comprising:
determining the motion vector field based on the 3D image registration, wherein the motion vector field is three-dimensional.

5. The method of claim 1, further comprising:
for each of the spatial points,
determining a first motion amplitude based on the corresponding motion vector of the first motion type; and
determining a second motion amplitude based on the corresponding motion vector of the second motion type,
wherein the temporal spread function is accessed based on the first motion amplitude and the second motion amplitude.

6. The method of claim 1, wherein the dual gating, based on the first motion signal and the second motion signal, the imaging data comprises:
dual gating, based on the first motion signal and the second motion signal, the imaging data based on a locally adaptive gating approach.

7. The method of claim 6, wherein the reconstructing an image from the dual gated imaging data and the temporal spread functions comprises:
determining an intra-frame motion amplitude based on a system intrinsic resolution; and
determining a gate number corresponding to the second motion signal according to the locally adaptive gating approach based on the intra-frame motion amplitude.

8. The method of claim 1, wherein the reconstructing an image from the dual gated imaging data and the temporal spread functions comprises:
determining a gating area corresponding to the first motion signal or the second motion signal;
determining a plurality of gate numbers for a plurality of voxels corresponding to spatial points represented in the gating area; and
determining the corresponding temporal spread functions for the plurality of voxels based on the plurality of gate numbers and the motion vectors of the spatial points corresponding to the first motion signal or the second motion signal.

9. The method of claim 8, wherein the determining the gating area comprises:
comparing the second motion amplitudes of the second motion type of the spatial points with a first threshold that relates to a system intrinsic resolution; and
determining the gating area based on the comparison.

10. A system for image processing, comprising:
a storage device storing instructions; and
a processor in communication with the storage, wherein when executing the instructions, the processor is caused to perform operations including:
a) obtaining imaging data acquired from a scanning of a subject;
b) obtaining a first motion signal of a first motion type;
c) obtaining a second motion signal of a second motion type;
d) dividing, based on the first motion signal, the imaging data into a plurality of groups of first gated imaging data, wherein a group of the first gated imaging data corresponds to a respective motion phase of the first motion type of the subject, a first group of the first gated imaging data corresponding to a first motion phase of the first motion type of spatial points of the subject and a second group of the first gated imaging data corresponding to a second motion phase of the first motion type of the spatial points of the subject;

e) reconstructing a first gated image corresponding to the first motion phase of the first motion type using the first group of the first gated imaging data and a second gated image corresponding to the second motion phase of the first motion type using the second group of the first gated imaging data;

f) determining a motion vector field of the first motion type by registering the first gated image and the second gated image, wherein the motion vector field of the first motion type includes a plurality of motion vectors of the first motion type, a motion vector of the first motion type indicating a motion of a respective spatial point of the first motion type from the first motion phase to the second motion phase;

g) dividing, based on the second motion signal, the imaging data into a plurality of groups of second gated imaging data, wherein a group of the second gated imaging data corresponds to a respective motion phase of the second motion type of the subject, a first group of the second gated imaging data corresponding to a first motion phase of the second motion type of the spatial points of the subject, and a second group of the second gated imaging data corresponding to a second motion phase of the second motion type of the spatial points of the subject;

h) obtaining a motion vector field of the second motion type by performing e) and f) with respect to the imaging data divided based on the second motion signal;

i) dual gating, based on the first motion signal and the second motion signal, the imaging data;

j) for each of the spatial points, assessing a temporal spread function based on the motion vector of the first motion type and the motion vector of the second motion type of the spatial point; and k) reconstructing an image from the dual gated imaging data and the temporal spread functions.

11. The system of claim 10, wherein the first motion type corresponds to a voluntary motion, and the second motion type corresponds to an involuntary motion.

12. The system of claim 10, wherein the determining the motion vector field of the first motion type by registering the first gated image and the second gated image includes:
performing a 2D image registration of the first gated image and the second gated image;
determining, for each of the spatial points, a 2D motion vector in a coronal plane and a 2D motion vector in a sagittal plane based on the registration; and
determining the motion vector field based on 2D motion vectors corresponding to the spatial points in the coronal plane and 2D motion vectors corresponding to the spatial points in the sagittal plane, wherein the motion vector field is three-dimensional.

13. The system of claim 10, wherein the registering the first gated image and the second gated image includes performing a 3D image registration, the method further comprising:
determining the motion vector field based on the 3D image registration, wherein the motion vector field is three-dimensional.

14. The system of claim 10, the operations further including:
for each of the spatial points,
determining a first motion amplitude based on the corresponding motion vector of the first motion type; and
determining a second motion amplitude based on the corresponding motion vector of the second motion type,
wherein the temporal spread function is accessed based on the first motion amplitude and the second motion amplitude.

15. The system of claim 10, wherein the dual gating, based on the first motion signal and the second motion signal, the imaging data comprises:
dual gating, based on the first motion signal and the second motion signal, the imaging data based on a locally adaptive gating approach.

16. The system of claim 15, wherein the reconstructing an image from the dual gated imaging data and the temporal spread functions comprises:
determining an intra-frame motion amplitude based on a system intrinsic resolution; and
determining a gate number corresponding to the second motion signal according to the locally adaptive gating approach based on the intra-frame motion amplitude.

17. The system of claim 10, wherein the reconstructing an image from the dual gated imaging data and the temporal spread functions comprises:
determining a gating area corresponding to the first motion signal or the second motion signal;
determining a plurality of gate numbers for a plurality of voxels corresponding to spatial points represented in the gating area; and
determining the corresponding temporal spread functions for the plurality of voxels based on the plurality of gate numbers and the motion vectors of the spatial points corresponding to the first motion signal or the second motion signal.

18. The system of claim 17, wherein the determining the gating area comprises:
comparing the second motion amplitudes of the second motion type of the spatial points with a first threshold that relates to a system intrinsic resolution; and
determining the gating area based on the comparison.

19. A non-transitory computer readable medium, comprising executable instructions that, when executed by at least one processor, direct the at least one processor to perform a method, the method comprising:

a) obtaining imaging data acquired from a scanning of a subject;

b) obtaining a first motion signal of a first motion type;

c) obtaining a second motion signal of a second motion type;

d) dividing, based on the first motion signal, the imaging data into a plurality of groups of first gated imaging data, wherein a group of the first gated imaging data corresponds to a respective motion phase of the first motion type of the subject, a first group of the first gated imaging data corresponding to a first motion phase of the first motion type of spatial points of the subject and a second group of the first gated imaging data corresponding to a second motion phase of the first motion type of the spatial points of the subject;

e) reconstructing a first gated image corresponding to the first motion phase of the first motion type using the first group of the first gated imaging data and a second gated image corresponding to the second motion phase of the first motion type using the second group of the first gated imaging data;
f) determining a motion vector field of the first motion type by registering the first gated image and the second gated image, wherein the motion vector field of the first motion type includes a plurality of motion vectors of the first motion type, a motion vector of the first motion type indicating a motion of a respective spatial point of the first motion type from the first motion phase to the second motion phase;
g) dividing, based on the second motion signal, the imaging data into a plurality of groups of second gated imaging data, wherein a group of the second gated imaging data corresponds to a respective motion phase of the second motion type of the subject, a first group of the second gated imaging data corresponding to a first motion phase of the second motion type of the spatial points of the subject and a second group of the second gated imaging data corresponding to a second motion phase of the second motion type of the spatial points of the subject;
h) obtaining a motion vector field of the second motion type by performing e) and f) with respect to the imaging data divided based on the second motion signal;
i) dual gating, based on the first motion signal and the second motion signal, the imaging data;
j) for each of the spatial points, assessing a temporal spread function based on the motion vector of the first motion type and the motion vector of the second motion type of the spatial point; and
k) reconstructing an image from the dual gated imaging data and the temporal spread functions.

20. The non-transitory computer readable medium of claim 19, wherein the first motion type corresponds to a voluntary motion, and the second motion type corresponds to an involuntary motion.

\* \* \* \* \*